United States Patent
Putnam et al.

(10) Patent No.: US 9,229,001 B2
(45) Date of Patent: Jan. 5, 2016

(54) METHOD AND APPARATUS FOR PERFORMING ASSAYS

(75) Inventors: Martin A. Putnam, Cheshire, CT (US); Alan D. Kersey, South Glastonbury, CT (US)

(73) Assignee: CYVEK, INC., Wallingford, CT (US)

( * ) Notice: Subject to any disclaimer, the term of this patent is extended or adjusted under 35 U.S.C. 154(b) by 702 days.

(21) Appl. No.: 13/511,593

(22) PCT Filed: Nov. 23, 2010

(86) PCT No.: PCT/US2010/057860
§ 371 (c)(1), (2), (4) Date: Sep. 24, 2012

(87) PCT Pub. No.: WO2011/063408
PCT Pub. Date: May 26, 2011

(65) Prior Publication Data
US 2013/0011859 A1    Jan. 10, 2013

Related U.S. Application Data

(60) Provisional application No. 61/263,572, filed on Nov. 23, 2009.

(51) Int. Cl.
G01N 33/543 (2006.01)
B01L 3/00 (2006.01)
G01N 35/10 (2006.01)

(52) U.S. Cl.
CPC .... G01N 33/54366 (2013.01); B01L 3/502715 (2013.01); B01L 3/502784 (2013.01);
(Continued)

(58) Field of Classification Search
CPC .................. G01N 33/54366; B01L 3/502715; B01L 3/502784; B01L 3/527
See application file for complete search history.

(56) References Cited

U.S. PATENT DOCUMENTS 3,555,143 A    1/1971    Axen et al.
3,867,517 A    2/1975    Ling
(Continued)

FOREIGN PATENT DOCUMENTS

CA    1189449    6/1985
DE    3226407    1/1984
(Continued)

OTHER PUBLICATIONS

Cooksey et al., "A vacuum manifold for rapid world-to-chip connectivity of complex PDMS microdevices," Lab on a Chip, vol. 9, No. 9 (Jan. 1, 2009).
(Continued)

*Primary Examiner* — Melanie Y Brown
(74) *Attorney, Agent, or Firm* — McCormick, Paulding & Huber LLP

(57) ABSTRACT

An apparatus is provided for performing an chemical, biochemical, or biological assay on a sample comprising: a microfluidic assay cartridge (1) that contains at least one sample inlet well (2) configured to receive a sample; and a microfluidic sub-unit (3) associated with the microfluidic assay cartridge (1) and comprising microfluidic channels (8), micro-valves (4, 4a, 9) and at least one separate and fluidicly-isolated isolation channel (5), and at least one hollow element (14); the at least one hollow element (14) being functionalized with a capture moiety or molecules (15) so as to form at least one reaction vessel (19); the microfluidic channels (8) and micro-valves (4, 4a, 9) configured to respond to signaling containing information about performing the assay and to controllably receive the sample and at least one reagent in the at least one reaction vessel (19), and to provide from the at least one reaction vessel (19) light containing information about the assay performed on the sample inside the at least one reaction vessel (19) as a result of said at least one reagent.

14 Claims, 17 Drawing Sheets

(52) U.S. Cl.
CPC ............. *G01N35/1097* (2013.01); *B01L 3/527* (2013.01); *B01L 2200/10* (2013.01); *B01L 2300/0636* (2013.01); *B01L 2400/0633* (2013.01)

(56) References Cited

U.S. PATENT DOCUMENTS

| | | | |
|---|---|---|---|
| 3,876,376 A | 4/1975 | Bauman et al. | |
| 3,939,350 A | 2/1976 | Kronick et al. | |
| 4,222,744 A | 9/1980 | McConnell | |
| 4,254,096 A | 3/1981 | Monthony et al. | |
| 4,368,047 A | 1/1983 | Andrade et al. | |
| 4,425,438 A | 1/1984 | Bauman et al. | |
| 4,447,546 A | 5/1984 | Hirschfeld | |
| 4,517,288 A | 5/1985 | Giegel et al. | |
| 4,690,907 A | 9/1987 | Hibino et al. | |
| 4,716,121 A | 12/1987 | Block et al. | |
| 4,717,545 A | 1/1988 | Morris | |
| 4,797,259 A | 1/1989 | Matkovich et al. | |
| 4,820,490 A | 4/1989 | Morris | |
| 4,844,869 A | 7/1989 | Glass | |
| 4,857,453 A | 8/1989 | Ullman et al. | |
| 4,923,819 A | 5/1990 | Fernandez et al. | |
| 5,004,923 A | 4/1991 | Hillman et al. | |
| 5,009,998 A | 4/1991 | Chow et al. | |
| 5,041,181 A | 8/1991 | Brackett et al. | |
| 5,118,608 A | 6/1992 | Layton et al. | |
| 5,164,598 A | 11/1992 | Hillman et al. | |
| 5,296,375 A | 3/1994 | Kricka et al. | |
| 5,302,349 A | 4/1994 | Dandliker et al. | |
| 5,304,487 A | 4/1994 | Wilding et al. | |
| 5,311,275 A | 5/1994 | Taniguchi et al. | |
| 5,376,252 A | 12/1994 | Ekstrom et al. | |
| 5,427,946 A | 6/1995 | Kricka et al. | |
| 5,500,350 A | 3/1996 | Baker et al. | |
| 5,508,200 A | 4/1996 | Tiffany et al. | |
| 5,512,151 A | 4/1996 | Hayamizu et al. | |
| 5,517,778 A | 5/1996 | Simson | |
| 5,534,328 A | 7/1996 | Ashmead et al. | |
| 5,593,290 A | 1/1997 | Greisch et al. | |
| 5,622,871 A | 4/1997 | May et al. | |
| 5,624,850 A | 4/1997 | Kumar et al. | |
| 5,637,469 A | 6/1997 | Wilding et al. | |
| 5,837,546 A | 11/1998 | Allen et al. | |
| 5,842,787 A | 12/1998 | Kopf-Sill et al. | |
| 5,856,174 A | 1/1999 | Lipshutz et al. | |
| 5,861,265 A | 1/1999 | Perry | |
| 5,866,345 A | 2/1999 | Wilding et al. | |
| 5,876,675 A | 3/1999 | Kennedy | |
| 5,882,465 A | 3/1999 | McReynolds | |
| 5,885,470 A | 3/1999 | Parce et al. | |
| 5,885,527 A * | 3/1999 | Buechler | 422/412 |
| 5,886,345 A | 3/1999 | Koster et al. | |
| 5,922,591 A | 7/1999 | Anderson et al. | |
| 5,932,799 A | 8/1999 | Moles | |
| 5,942,443 A | 8/1999 | Parce et al. | |
| 5,965,237 A | 10/1999 | Bruin et al. | |
| 5,976,896 A | 11/1999 | Kumar et al. | |
| 6,008,057 A | 12/1999 | Glass et al. | |
| 6,020,209 A | 2/2000 | Narang et al. | |
| 6,046,056 A | 4/2000 | Parce et al. | |
| 6,048,498 A | 4/2000 | Kennedy | |
| 6,068,751 A | 5/2000 | Neukermans | |
| 6,068,752 A | 5/2000 | Dubrow et al. | |
| 6,073,482 A | 6/2000 | Moles | |
| 6,082,185 A | 7/2000 | Saaski | |
| 6,083,763 A | 7/2000 | Balch | |
| 6,086,740 A | 7/2000 | Kennedy | |
| 6,103,537 A | 8/2000 | Ullman et al. | |
| 6,143,152 A | 11/2000 | Simpson et al. | |
| 6,167,910 B1 | 1/2001 | Chow | |
| 6,197,595 B1 | 3/2001 | Anderson et al. | |
| 6,214,560 B1 | 4/2001 | Yguerabide et al. | |
| 6,235,241 B1 | 5/2001 | Catt et al. | |
| 6,238,538 B1 | 5/2001 | Parce et al. | |
| 6,245,296 B1 | 6/2001 | Ligler et al. | |
| 6,251,343 B1 | 6/2001 | Dubrow et al. | |
| 6,267,858 B1 | 7/2001 | Parce et al. | |
| 6,274,337 B1 | 8/2001 | Parce et al. | |
| 6,293,012 B1 | 9/2001 | Moles | |
| 6,306,669 B1 | 10/2001 | Yano et al. | |
| 6,321,791 B1 | 11/2001 | Chow | |
| 6,361,958 B1 | 3/2002 | Shieh et al. | |
| 6,366,924 B1 | 4/2002 | Parce | |
| 6,383,748 B1 | 5/2002 | Carpay et al. | |
| 6,391,622 B1 | 5/2002 | Knapp et al. | |
| 6,408,878 B2 | 6/2002 | Unger et al. | |
| 6,479,299 B1 | 11/2002 | Parce et al. | |
| 6,494,230 B2 | 12/2002 | Chow | |
| 6,497,155 B1 | 12/2002 | Feygin et al. | |
| 6,507,989 B1 | 1/2003 | Bowden et al. | |
| 6,517,778 B1 | 2/2003 | Kumar et al. | |
| 6,520,753 B1 | 2/2003 | Grosjean et al. | |
| 6,524,830 B2 | 2/2003 | Kopf-Sill et al. | |
| 6,532,997 B1 | 3/2003 | Bedingham et al. | |
| 6,533,914 B1 | 3/2003 | Liu | |
| 6,534,013 B1 | 3/2003 | Kennedy | |
| 6,541,213 B1 | 4/2003 | Weigl et al. | |
| 6,551,841 B1 | 4/2003 | Wilding et al. | |
| 6,576,478 B1 | 6/2003 | Wagner et al. | |
| 6,648,015 B1 | 11/2003 | Chow | |
| 6,649,358 B1 | 11/2003 | Parce et al. | |
| 6,649,403 B1 | 11/2003 | McDevitt et al. | |
| 6,680,206 B1 | 1/2004 | McDevitt et al. | |
| 6,719,868 B1 | 4/2004 | Schueller et al. | |
| 6,729,352 B2 | 5/2004 | O'Connor et al. | |
| 6,747,285 B2 | 6/2004 | Schueller et al. | |
| 6,756,019 B1 | 6/2004 | Dubrow et al. | |
| 6,767,194 B2 | 7/2004 | Jeon et al. | |
| 6,767,706 B2 | 7/2004 | Quake et al. | |
| 6,875,619 B2 | 4/2005 | Blackburn | |
| 6,908,737 B2 | 6/2005 | Ravkin et al. | |
| 6,908,770 B1 | 6/2005 | McDevitt et al. | |
| 6,929,030 B2 | 8/2005 | Unger et al. | |
| 6,960,467 B2 | 11/2005 | Shieh et al. | |
| 6,994,826 B1 | 2/2006 | Hasselbrink, Jr. et al. | |
| 7,005,292 B2 | 2/2006 | Wilding et al. | |
| 7,018,830 B2 | 3/2006 | Wilding et al. | |
| 7,028,536 B2 | 4/2006 | Karp et al. | |
| 7,033,476 B2 | 4/2006 | Lee et al. | |
| 7,040,338 B2 | 5/2006 | Unger et al. | |
| 7,087,181 B2 | 8/2006 | Schmidt et al. | |
| 7,122,153 B2 | 10/2006 | Ho | |
| 7,125,510 B2 | 10/2006 | Huang | |
| 7,128,910 B2 | 10/2006 | Tucker et al. | |
| 7,143,785 B2 | 12/2006 | Maerkl et al. | |
| 7,144,616 B1 | 12/2006 | Unger et al. | |
| 7,164,533 B2 | 1/2007 | Moon et al. | |
| 7,186,383 B2 | 3/2007 | Webster et al. | |
| 7,189,358 B2 | 3/2007 | Beach et al. | |
| 7,192,559 B2 | 3/2007 | Chow et al. | |
| 7,192,629 B2 | 3/2007 | Lammertink et al. | |
| 7,216,671 B2 | 5/2007 | Unger et al. | |
| 7,238,269 B2 | 7/2007 | Gason et al. | |
| 7,241,421 B2 | 7/2007 | Webster et al. | |
| 7,250,128 B2 | 7/2007 | Unger et al. | |
| 7,258,837 B2 | 8/2007 | Yager et al. | |
| 7,285,411 B1 | 10/2007 | Parce et al. | |
| 7,294,503 B2 | 11/2007 | Quake et al. | |
| 7,326,561 B2 | 2/2008 | Goodman et al. | |
| 7,343,248 B2 | 3/2008 | Parce et al. | |
| 7,349,158 B2 | 3/2008 | Moon et al. | |
| 7,351,376 B1 | 4/2008 | Quake et al. | |
| 7,378,280 B2 | 5/2008 | Quake et al. | |
| 7,396,674 B2 | 7/2008 | Miyakawa et al. | |
| 7,399,643 B2 | 7/2008 | Moon et al. | |
| 7,419,639 B2 | 9/2008 | Osterfeld et al. | |
| 7,445,926 B2 | 11/2008 | Mathies et al. | |
| 7,473,562 B2 | 1/2009 | Van Beuningen et al. | |
| 7,476,363 B2 | 1/2009 | Unger et al. | |
| 7,491,552 B2 | 2/2009 | McDevitt et al. | |
| 7,507,588 B2 | 3/2009 | Mehrpouyan et al. | |
| 7,622,081 B2 | 11/2009 | Chou et al. | |
| 7,622,083 B2 | 11/2009 | Amirkhanian et al. | |

(56) References Cited

U.S. PATENT DOCUMENTS

| | | | |
|---|---|---|---|
| 7,682,565 B2 | 3/2010 | Linton et al. |
| 7,682,817 B2 | 3/2010 | Cohen et al. |
| 7,691,333 B2 | 4/2010 | McBride et al. |
| 7,695,683 B2 | 4/2010 | Quan et al. |
| 7,736,890 B2 | 6/2010 | Sia et al. |
| 7,736,891 B2 | 6/2010 | Nelson et al. |
| 7,745,207 B2 | 6/2010 | Jovanovich et al. |
| 7,754,010 B2 | 7/2010 | Unger et al. |
| 7,766,033 B2 | 8/2010 | Mathies et al. |
| 7,799,553 B2 | 9/2010 | Mathies et al. |
| 7,833,708 B2 | 11/2010 | Enzelberger et al. |
| 7,837,946 B2 | 11/2010 | McBride et al. |
| 7,843,567 B2 | 11/2010 | Moon et al. |
| 7,887,750 B2 | 2/2011 | Blatt et al. |
| 7,887,753 B2 | 2/2011 | Quake et al. |
| 7,892,493 B2 | 2/2011 | Weekamp |
| 7,919,172 B2 | 4/2011 | Schueller et al. |
| 7,935,489 B2 | 5/2011 | O'Neill et al. |
| 7,943,089 B2 | 5/2011 | Yang et al. |
| 7,947,492 B2 * | 5/2011 | Niehaus ................. 435/288.7 |
| 8,049,893 B2 | 11/2011 | Moon et al. |
| 8,101,403 B2 | 1/2012 | Yager et al. |
| 8,124,015 B2 | 2/2012 | Diercks et al. |
| 8,129,176 B2 | 3/2012 | Quake et al. |
| 8,147,774 B2 | 4/2012 | Hagiwara et al. |
| 8,168,139 B2 | 5/2012 | Manger et al. |
| 8,211,657 B2 | 7/2012 | Li et al. |
| 8,236,573 B2 | 8/2012 | Tokhtuev et al. |
| 8,277,759 B2 | 10/2012 | Sundberg et al. |
| 2001/0005489 A1 | 6/2001 | Roach et al. |
| 2002/0081744 A1* | 6/2002 | Chan et al. .................. 436/94 |
| 2002/0102742 A1 | 8/2002 | Parce et al. |
| 2002/0144738 A1 | 10/2002 | Unger et al. |
| 2002/0187560 A1 | 12/2002 | Pezzuto et al. |
| 2003/0012693 A1 | 1/2003 | Otillar et al. |
| 2003/0032191 A1 | 2/2003 | Hilson et al. |
| 2003/0054376 A1 | 3/2003 | Mullis et al. |
| 2003/0185713 A1 | 10/2003 | Leonard et al. |
| 2004/0101444 A1 | 5/2004 | Sommers et al. |
| 2004/0110199 A1 | 6/2004 | Montemagno et al. |
| 2004/0126875 A1 | 7/2004 | Putnam et al. |
| 2004/0189311 A1 | 9/2004 | Glezer et al. |
| 2004/0200909 A1 | 10/2004 | McMillan et al. |
| 2004/0219661 A1 | 11/2004 | Chen et al. |
| 2004/0228770 A1 | 11/2004 | Gandhi et al. |
| 2005/0098750 A1 | 5/2005 | Sobek |
| 2005/0100943 A1 | 5/2005 | Kambara et al. |
| 2005/0214173 A1 | 9/2005 | Facer et al. |
| 2005/0221385 A1 | 10/2005 | Nikiforov et al. |
| 2005/0266582 A1 | 12/2005 | Modlin et al. |
| 2006/0057576 A1 | 3/2006 | Paszkowski et al. |
| 2006/0063271 A1 | 3/2006 | Putnam et al. |
| 2006/0073484 A1 | 4/2006 | Mathies et al. |
| 2006/0076068 A1 | 4/2006 | Young et al. |
| 2006/0207877 A1 | 9/2006 | Schmidt et al. |
| 2006/0233668 A1 | 10/2006 | Resch-Genger et al. |
| 2006/0257956 A1 | 11/2006 | Basset et al. |
| 2006/0263818 A1 | 11/2006 | Scherer et al. |
| 2006/0263914 A1 | 11/2006 | Sando et al. |
| 2006/0289059 A1 | 12/2006 | Krylov et al. |
| 2007/0017633 A1* | 1/2007 | Tonkovich et al. ........... 156/300 |
| 2007/0149863 A1 | 6/2007 | Padmanabhan |
| 2007/0224084 A1 | 9/2007 | Holmes et al. |
| 2007/0248958 A1 | 10/2007 | Jovanovich et al. |
| 2008/0017512 A1 | 1/2008 | Bordunov et al. |
| 2008/0035499 A1* | 2/2008 | Weng ............................ 206/229 |
| 2008/0131327 A1 | 6/2008 | Van Dam |
| 2008/0241858 A1 | 10/2008 | Metzger et al. |
| 2008/0280285 A1 | 11/2008 | Chen et al. |
| 2008/0311585 A1 | 12/2008 | Gao et al. |
| 2008/0311665 A1 | 12/2008 | Ryan et al. |
| 2009/0071833 A1* | 3/2009 | Gorfinkel et al. ............. 204/601 |
| 2009/0074623 A1 | 3/2009 | Park et al. |
| 2009/0087884 A1 | 4/2009 | Beerling et al. |
| 2009/0148933 A1 | 6/2009 | Battrell et al. |
| 2009/0181411 A1 | 7/2009 | Battrell et al. |
| 2009/0215158 A1 | 8/2009 | Sekizawa et al. |
| 2009/0253181 A1 | 10/2009 | Vangbo et al. |
| 2009/0257920 A1 | 10/2009 | Facer et al. |
| 2009/0325171 A1 | 12/2009 | Hirt et al. |
| 2009/0325276 A1 | 12/2009 | Battrell et al. |
| 2010/0101670 A1 | 4/2010 | Juncker et al. |
| 2010/0167384 A1 | 7/2010 | Clemmens et al. |
| 2010/0173394 A1 | 7/2010 | Colston, Jr. et al. |
| 2010/0186841 A1 | 7/2010 | Mukaddam et al. |
| 2010/0216248 A1 | 8/2010 | Wardlaw |
| 2010/0221814 A1 | 9/2010 | Asogawa et al. |
| 2010/0233791 A1 | 9/2010 | Sim et al. |
| 2010/0303687 A1 | 12/2010 | Blaga et al. |
| 2011/0008776 A1* | 1/2011 | Warthoe et al. ................... 435/6 |
| 2011/0020947 A1 | 1/2011 | Bedingham et al. |
| 2011/0105361 A1 | 5/2011 | Moon et al. |
| 2011/0195260 A1 | 8/2011 | Lee et al. |
| 2011/0262940 A1 | 10/2011 | Hisamoto et al. |
| 2011/0306081 A1 | 12/2011 | Szita et al. |
| 2012/0164036 A1 | 6/2012 | Stern et al. |
| 2012/0266986 A1 | 10/2012 | Wimberger-Friedl et al. |

FOREIGN PATENT DOCUMENTS

| | | |
|---|---|---|
| EP | 0401033 | 12/1990 |
| EP | 1415788 | 5/2004 |
| EP | 1404448 | 9/2006 |
| EP | 1936382 | 6/2008 |
| EP | 2284538 | 2/2011 |
| EP | 2463666 | 6/2012 |
| GB | 2155152 | 9/1985 |
| GR | 94100467 | 6/1996 |
| JP | 09288089 | 11/1997 |
| JP | 2001-157855 | 6/2001 |
| JP | 2003-507737 | 2/2003 |
| JP | 2005-140681 | 6/2005 |
| JP | 2007-516419 | 6/2007 |
| RO | 122612 | 9/2009 |
| WO | 92/04613 | 3/1992 |
| WO | 97/37803 | 10/1997 |
| WO | 9911754 | 3/1999 |
| WO | 9944217 | 9/1999 |
| WO | 01/07889 | 2/2001 |
| WO | 01/14865 | 3/2001 |
| WO | 03004160 | 1/2003 |
| WO | 03042677 | 5/2003 |
| WO | 2004/000721 | 12/2003 |
| WO | 2004/034028 | 4/2004 |
| WO | 2004/041061 | 5/2004 |
| WO | 2004/059299 | 7/2004 |
| WO | 2004/061085 | 7/2004 |
| WO | 2005/066613 | 7/2005 |
| WO | 2005/107938 | 11/2005 |
| WO | 2006/071470 | 7/2006 |
| WO | 2007/021813 | 2/2007 |
| WO | 2007/032316 | 3/2007 |
| WO | 2007/033385 | 3/2007 |
| WO | 2007/044091 | 4/2007 |
| WO | 2007/092713 | 8/2007 |
| WO | 2007/093939 | 8/2007 |
| WO | 2007/106579 | 9/2007 |
| WO | 2007/117987 | 10/2007 |
| WO | 2007/136715 | 11/2007 |
| WO | 2008/032128 | 3/2008 |
| WO | 2008/043046 | 4/2008 |
| WO | 2008/075253 | 6/2008 |
| WO | 2008/089493 | 7/2008 |
| WO | 2008/115626 | 9/2008 |
| WO | 2008/154036 | 12/2008 |
| WO | 2009/012340 | 1/2009 |
| WO | 2009/029177 | 3/2009 |
| WO | 2009/088408 | 7/2009 |
| WO | 2009/105711 | 8/2009 |
| WO | 2010/017210 | 2/2010 |
| WO | 2010/027812 | 3/2010 |
| WO | 2010/057078 | 5/2010 |
| WO | 2010/077618 | 7/2010 |
| WO | 2010/148252 | 12/2010 |

(56) References Cited

FOREIGN PATENT DOCUMENTS

| | | |
|---|---|---|
| WO | 2011/040884 | 4/2011 |
| WO | 2011/053845 | 5/2011 |
| WO | 2012/129455 | 9/2012 |

OTHER PUBLICATIONS

Grover et al., "Teflon films for chemically-inert microfluidic valves and pumps," Lab on a Chip, vol. 8, No. 6 (Jan. 1, 2008).

Hicks, Jocelyn M., "Fluorescence Immunoassay," from "Human Pathology", vol. 15, No. 2, Feb. 1984, pp. 112-116 (5 pages).

Fayram, Sandra L., "Fluorescence Immunoassay and Passive Latex Agglutination as Alternatives to Hemagglutination Inhibition for Determining Rubella Immune Status," from "Journal of Clinical Microbiology," vol. 17, No. 4, Apr. 3, 1983, pp. 685-688 (4 pages).

Ozinskas, Alvydas J., "Principles of Fluorescence Immunoassay," from "Topics in Fluorescence Spectroscopy, vol. 4: Probe Design and Chemical Sensing," 1994, pp. 449-496 (48 pages).

Japanese Office Action; JP 2012-540157; Aug. 6, 2013; 7 pp.

Chaudhury and Whitesides, 1991, "Direct Measurement of Interfacial Interactions Between Semispherical Lenses and Flat Sheets of Poly(dimethylsiloxane) and Their Chemical Derivatives", p. 1021: Interaction between Oxidized PDMS Surfaces.

Delamarche et al, "Patterned Delivery of Immunoglobulins to Surfaces Using Microfluidic Networks", Science, vol. 276, p. 779-781, (submitted Dec. 30, 1996).

Duffy, et al, "Rapid Prototyping of Microfluidic Systems in Poly (dimethylsiloxane)", Anal. Chem vol. 70, No. 23,1998, 4974-4984.

Effenhauser et al, "Integrated Capillary Electrophoresis on Flexible Silcione Microdevices; Analysis of DNA . . . ", Analytical Chemistry, vol. 69, No. 17, 3451-7.

Folta et al, "Design, Fabrication and Testing of a Miniature Peristaltic Membrane Pump", 1992, Technical Digest IEEE Solid-State Sensors and Actuators Workshop, pp. 186-189.

Fujii et al., Bulk- and Surface-Modified Combinable PDMS Capillary Sensor Array as an Easy-to-Use Sensing Device with Enhanced Sensitivity to Elevated Concentrations of Multiple Serum Sample Components, Lab Chip 12:1522 (2012).

Henares et al., "Current Development in Microfluidic Immunosensing Chip," Analytica Chimica Acta 611:17-30 (2008).

Henares et al., "Development of Single-Step Heterogenous Sandwich Capillary Immunosensor for Capillary-Assembled Microchip (CAs-CHIP) Integration," Twelfth International Conference on Miniaturized Systems for Chemistry and Life Sciences, San Diego, California (Oct. 12-16, 2008).

Henares et al., "Enzyme-Release Capillary as a Facile Enzymatic Biosensing Part for a Capillary-Assembled Microchip," Analytical Sciences 25:1025-1028(Aug. 2009).

Henares et al., "Multiple Enzyme Linked Immunosorbent Assay System on a Capillary-Assembled Microchip Integrating Valving and Immuno-Reaction Functions," Analytica Chimica Acta 589:173-179 (2007).

Henares et al., "Single-Drop Analysis of Various Proteases in a Cancer Cell Lysate Using a Capillary-Assembled Microchip," Anal Bioanal Chem 391:2507-2512 (2008).

Henares et al., "Single-Step ELISA Capillary Sensor Based on Surface-Bonded Glucose Oxidase, Antibody, and Physically-Adsorbed PEG Membrane Containing Peroxidase-Labeled Antibody," Sensors and Actuators B 149:319-324 (2010).

Hisamoto et al., "Capillary-Assembled Microchip as an On-Line Deproteinization Device for Capillary Electrophoresis," Anal Bioanal Chem 386:733-738 (2006).

Hisamoto et al., "Capillary-Assembled Microchip for Universal Integration of Various Chemical Functions onto a Single Microfluidic Device," Anal. Chem. 76:3222-3228 (2004).

Hisamoto et al., "Integration of Multiple-Ion-Sensing on a Capillary-Assembled Microchip," Analytica Chimica Acta 556:164-170 (2006).

Hisamoto et al., "Integration of Valving and Sensing on a Capillary-Assembled Microchip," Anal. Chem. 77:2266-2271 (2005).

Hosokawa, K. and Maeda, R., "A normally closed PDMS (polydimethylsiloxane) microvalve", T.IEE Japan, vol. 120-E, No. 4, 2000.

Hosokawa, K, and Maeda, R., "A pneumatically-actuated three-way microvalve fabricated with polydimethysiloxane using the membrane transfer technique", J. Mickromecjh. Microeng. 10 (2000) 415-420.

Lammerink, et al "Modular Concept for Fluid Handling Systems—A demonstrator Micro Analysis System", 1996, Proc. IEEE Micro Electro Mechanical Systgems Workshop, San Diego CA, Feb. 1996, pp. 389-394.

Macdonald and Whitesides, "Poly(dimethylsilocane) as a Material for Fabricating Microfluidic Devices", 2002.

Madou, Fundamentals of Microfabrication, CRC Press, 1997, pp. 382-394 especially p. 390.

Shoji et al, "Microflow Devices and Systems", 1994, J. Micromech. Microeng. 4 (1994) 157-171.

Smits, "Piezoelectric Micropump with Three Valves Working Peristaltically", 1990, Sensors and Actuators, A21-23 (1990) 203-206.

Yacoub-George et al., "Automated 10-Channel Capillary Chip Immunodetector for Biological Agents Detection," Biosensors and Bioelectronics 22:1368-1375 (2007).

Supplementary European Search Report from corresponding European Appn. No. 10832371.8 dated Jul. 22, 2013.

Supplementary European Search Report dated Nov. 5, 2014 for Application No. 12760266.2.

European Communication dated Nov. 21, 2014 for Application No. 12760266.2.

* cited by examiner

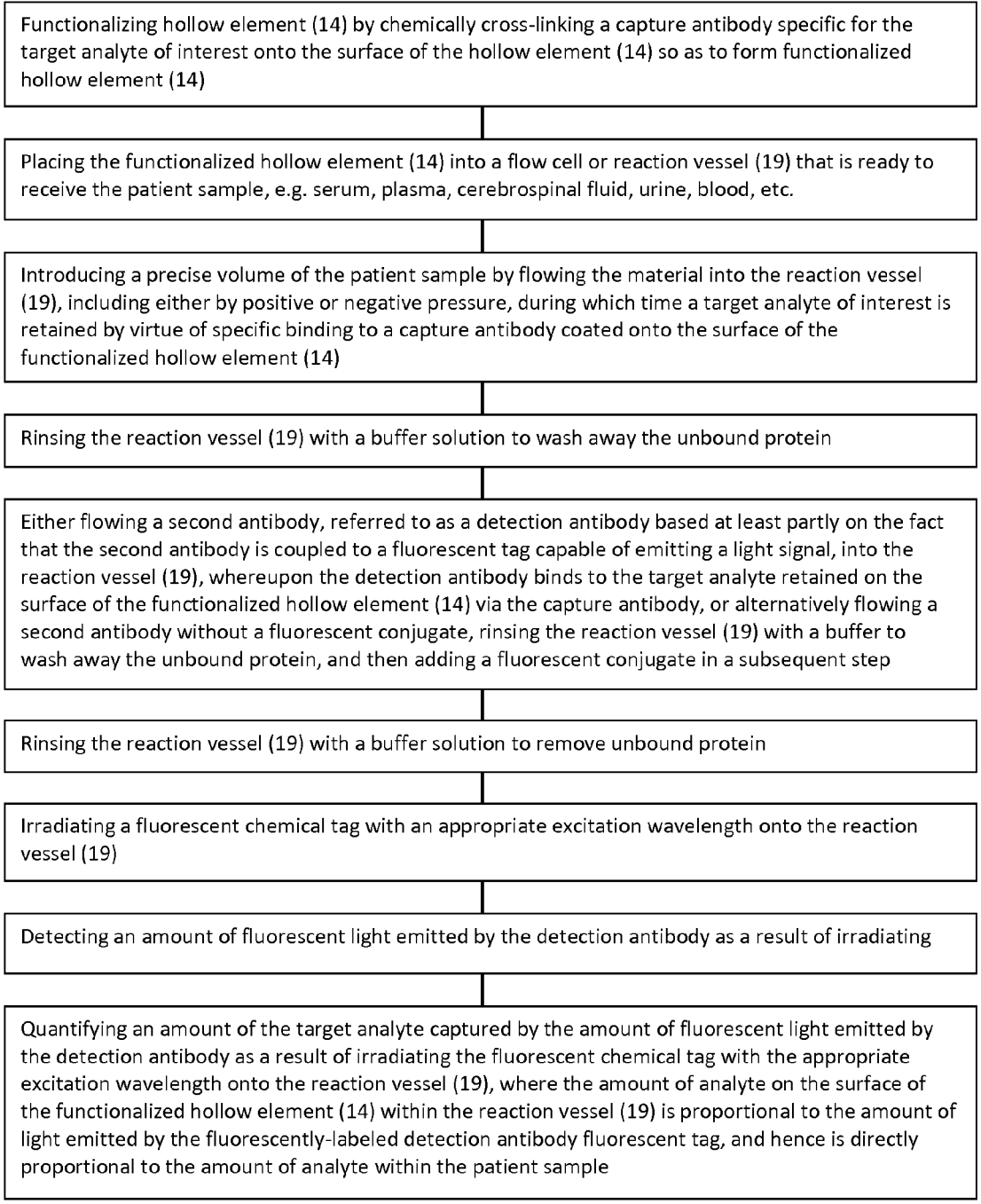
Figure 1(c): A METHOD FOR PERFORMING A BIOLOGICAL ASSAY:

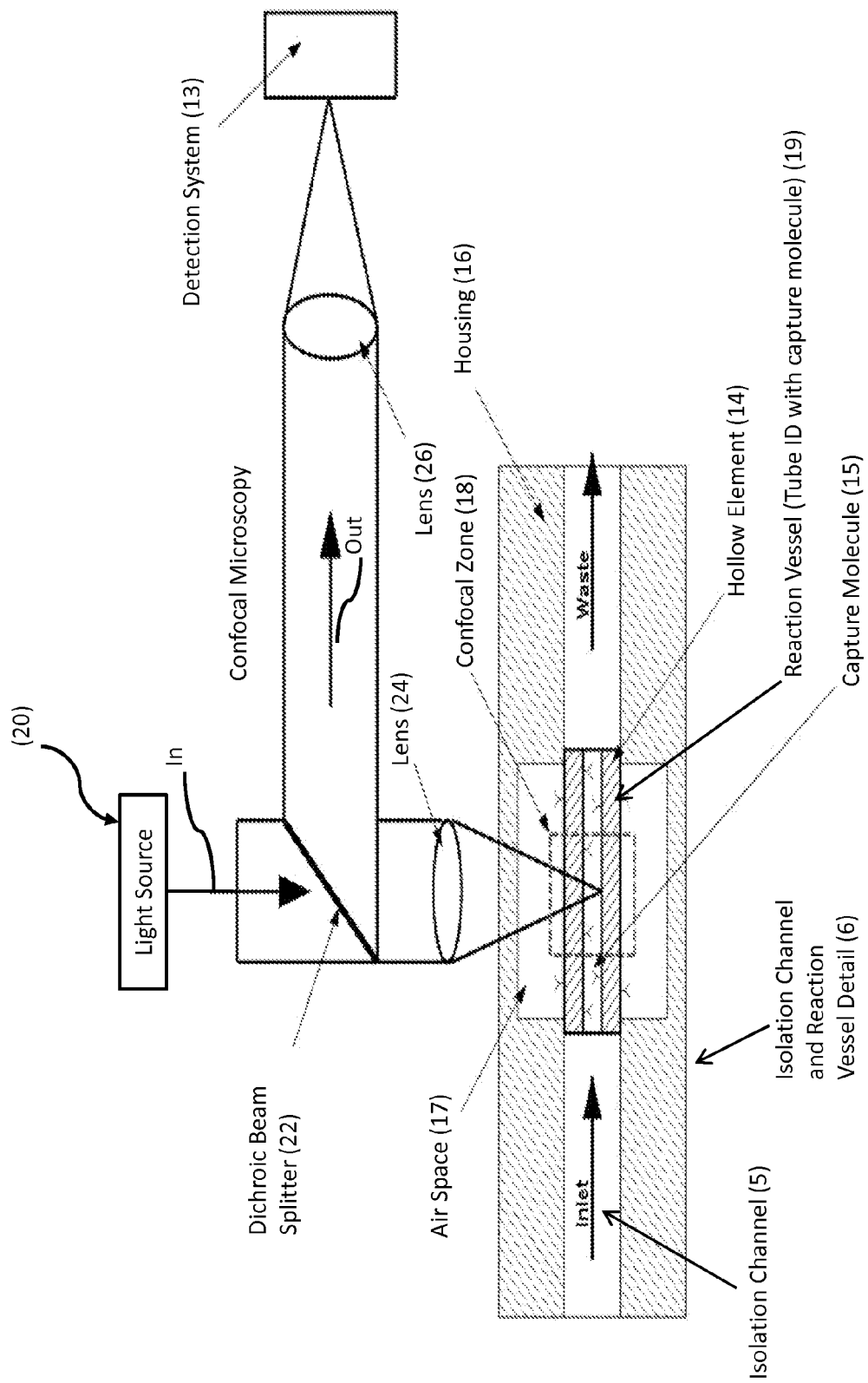
Figure 2: Isolation Channel and Reaction Vessel Detail (6)

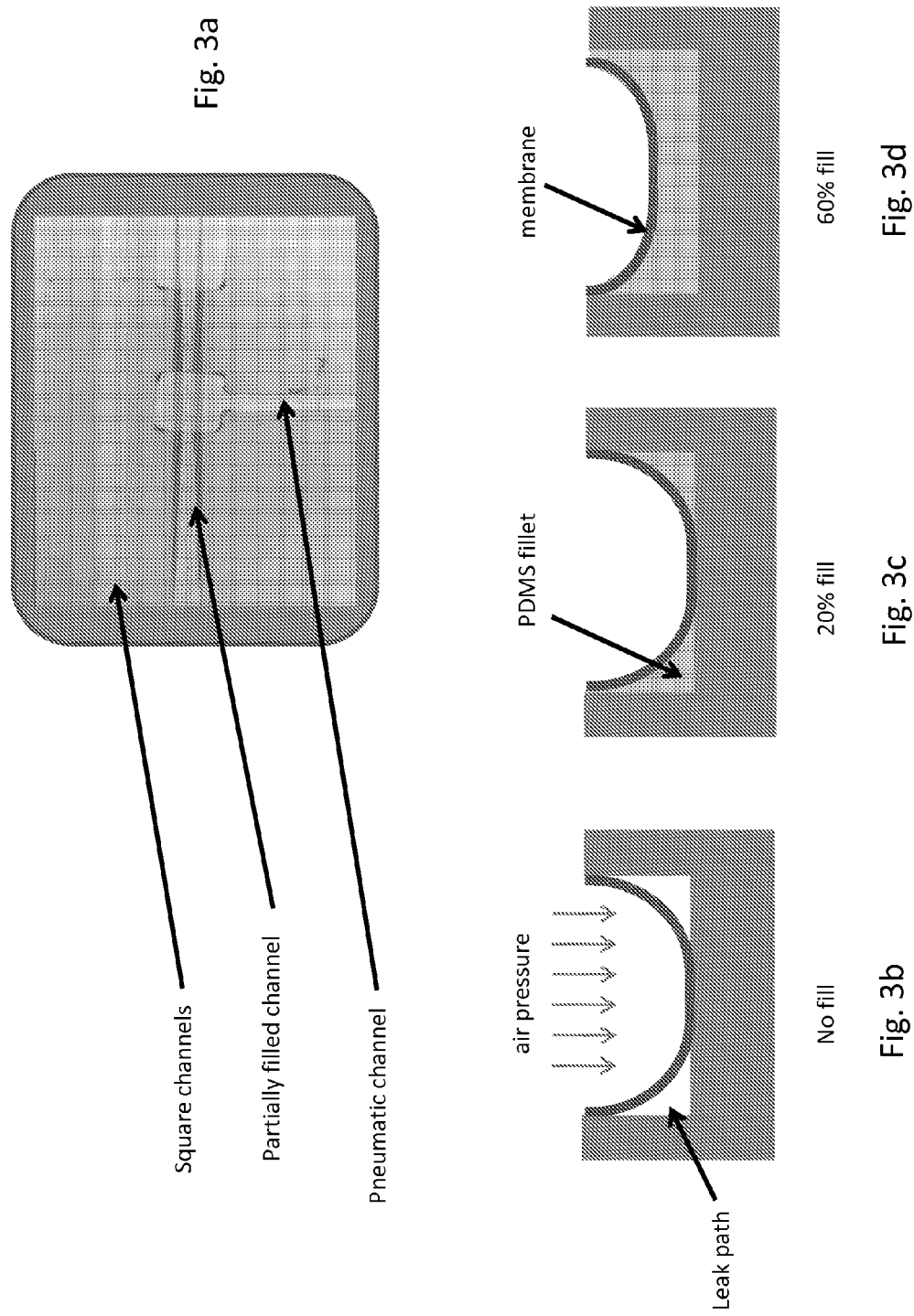
Figure 3: Channel Geometry

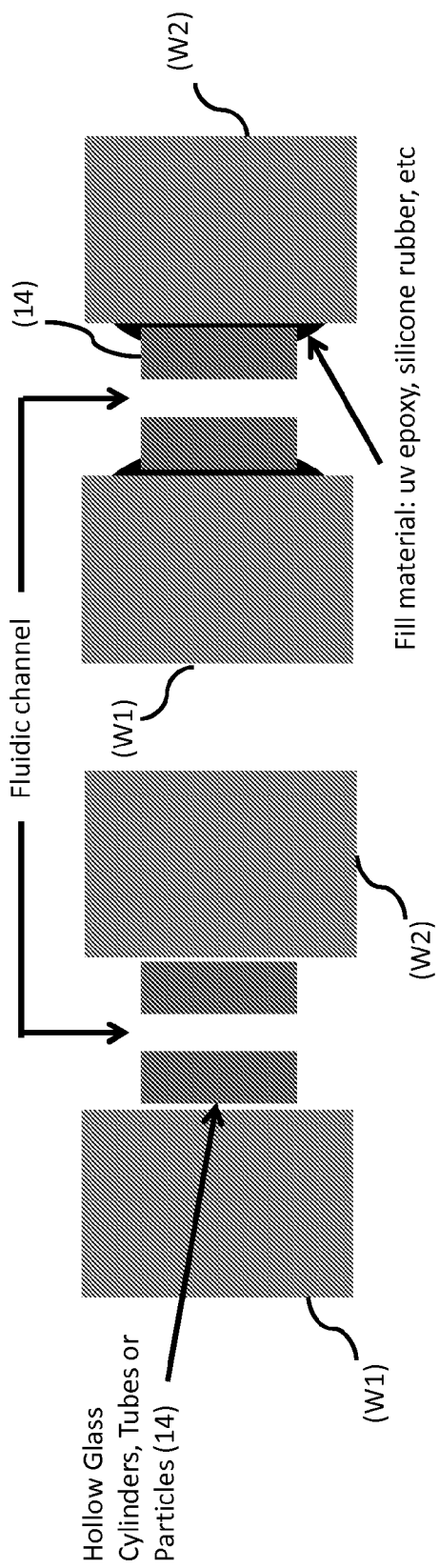
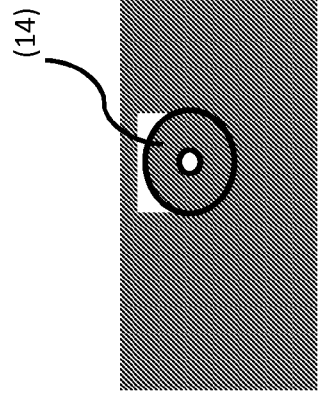

| Epoxy | Type | Viscosity | Dispensable | Fluor | Cure Method | Comment | Acceptable |
|---|---|---|---|---|---|---|---|
| Dymax 921 Gel | uv curable epoxy | 25,000 | yes | high | uv/thermal | good viscosity but very high fluorescence | no |
| Loctitie 3211 | uv curable epoxy | 10,000 | yes | med | uv | med fluorescence | no |
| Dymax 9622 | uv curable epoxy | 12,000 | yes | low | uv | low fluorescence | yes |
| Sylgard 184 | silicone encaspsalent | 3,900 | yes | low | thermal | 24hr at RT, viscosity too low | yes |
| Sylgard 186 | silicone encaspsalent | 7,800 | yes | low | thermal | 24hr at RT, viscosity too low | yes |
| RTV 118 | RTV silicone adhesive | ~25,000 | yes | low | thermal | cures in tip ~ 30 min, clarity is questionalble | maybe |
| "Clear RTV" | RTV silicone adhesive | ~40,000 | yes | low | thermal | very thick and cures in tip | no |
| Nusil CF15-2186 | silicone elastomer | 80,000 | TBD | TBD | 24 hr - RT | | TBD |
| Nusil R31-2186 | RTV silicone adhesive | 80,000 | TBD | TBD | 24 hr - RT | | TBD |
| Nusil R33-2186 | silicone adhesive | 80,000 | TBD | TBD | 24 hr - RT | | TBD |
| Nusil LS1-6941 | LSR adhesive | 75,000 | TBD | Low | 30 min @ 75C | will RT cure | TBD |
| Nusil LS-6946 | Optically elastomer | 40,000 | TBD | TBD | 30 min @ 75C | will RT cure | TBD |
| Dyamx 9621 | uv curable epoxy | 20,000 | TBD | Low | uv | | TBD |

Fig. 3g: Epoxy down select matrix

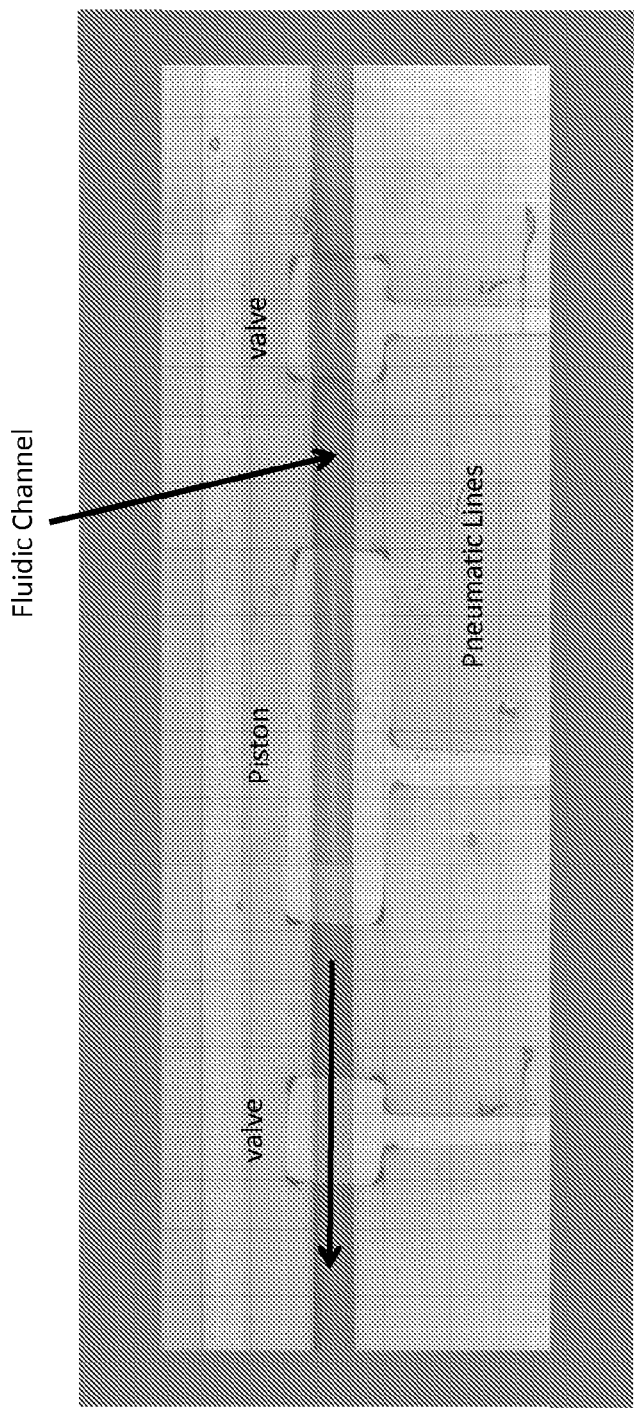
Figure 4: Pneumatically Actuated Pump

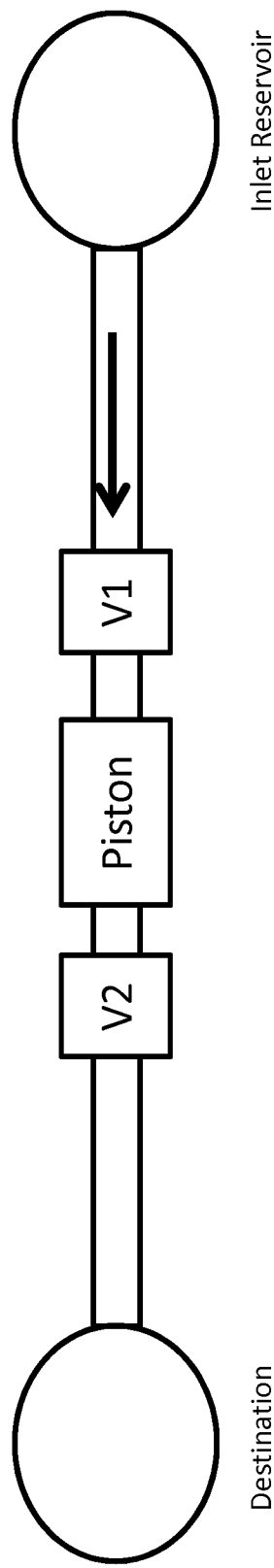
Figure 5: Pump Operation

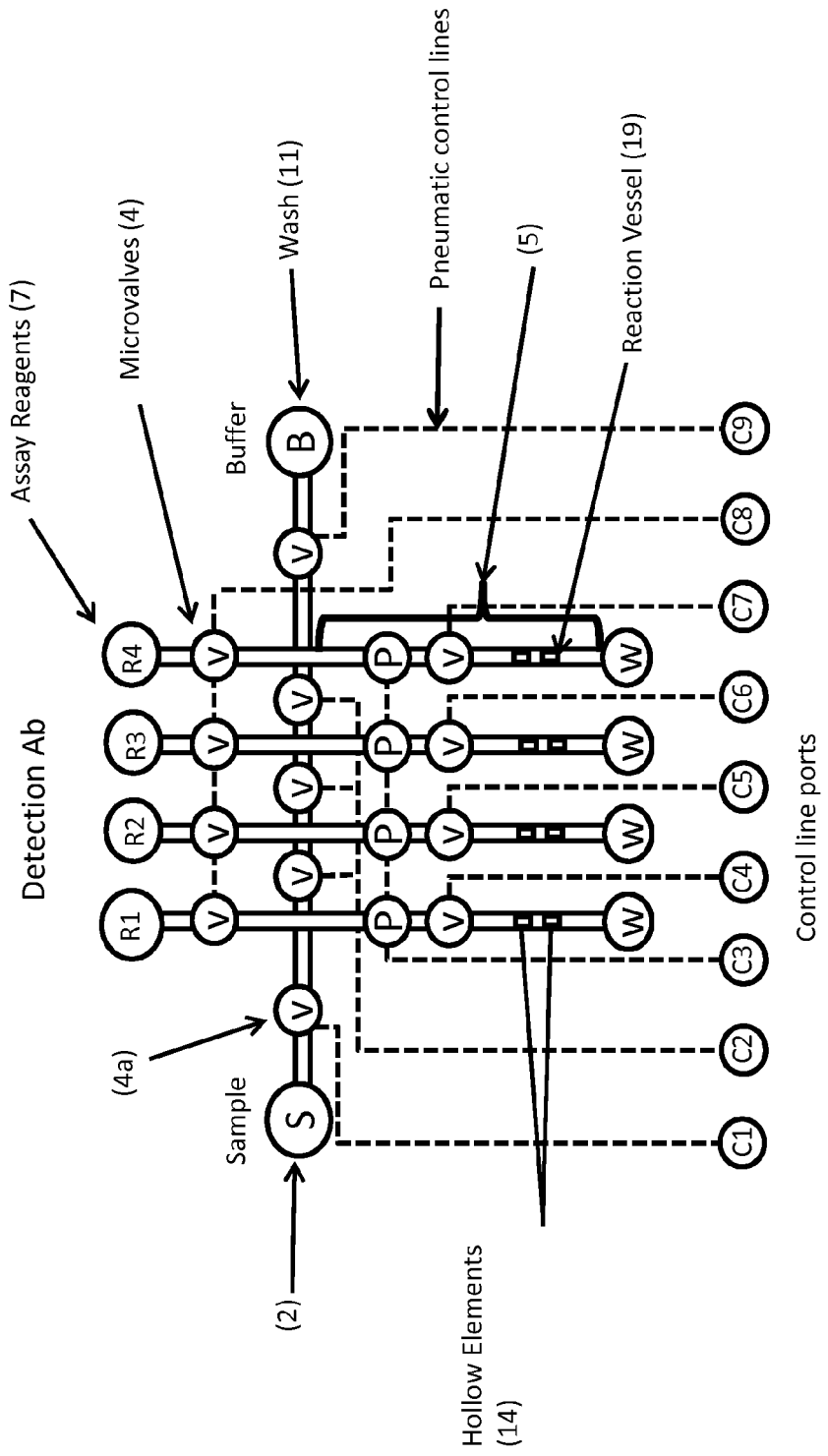
Figure 6: Multiplex Architecture Independent channel pumping
Fig. 6a(1): 4 plex architecture with independent pump control and individual waste reservoirs.

NC (vac actuated) states for buffer pumping (1 complete cycle)

| Cycle | 1 | 2 | 3 | 4 | 5 | 6 | 7 | 8 | 9 |
|---|---|---|---|---|---|---|---|---|---|
| 1 | 0 | 0 | 0 | 0 | 0 | 0 | 0 | 0 | 0 |
| 2 | 0 | 1 | 0 | 0 | 0 | 0 | 0 | 0 | 1 |
| 3 | 0 | 1 | 1 | 0 | 0 | 0 | 0 | 0 | 1 |
| 4 | 0 | 1 | 1 | 0 | 0 | 0 | 1 | 0 | 1 |
| 5 | 0 | 1 | 1 | 0 | 0 | 0 | 1 | 1 | 0 |
| 6 | 0 | 1 | 0 | 0 | 0 | 0 | 1 | 0 | 0 |
| 7 | 0 | 1 | 0 | 0 | 0 | 0 | 0 | 0 | 0 |

Fig. 6a(2)

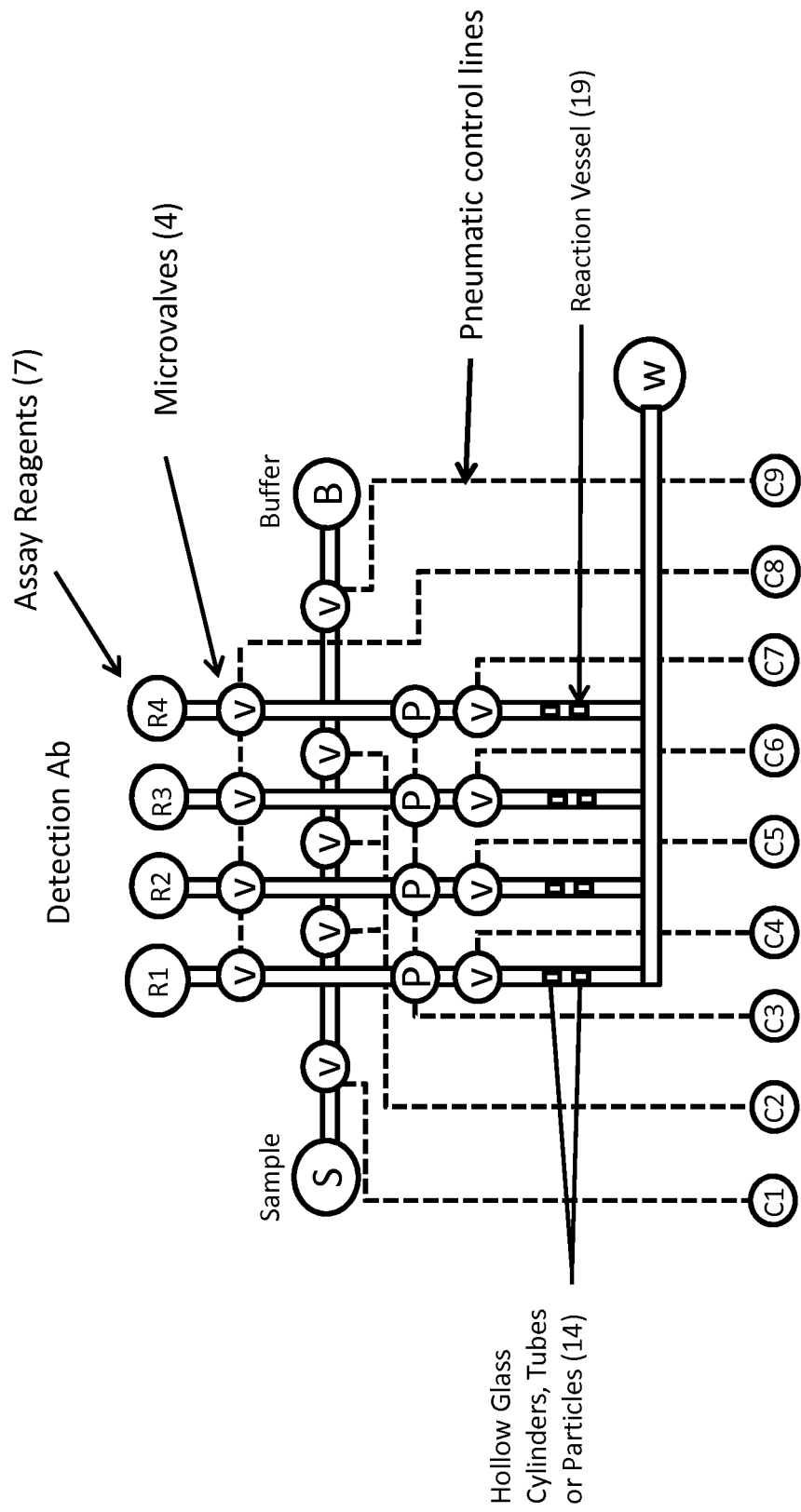
Fig. 6b: 4 plex architecture with independent pump control and common waste reservoir.

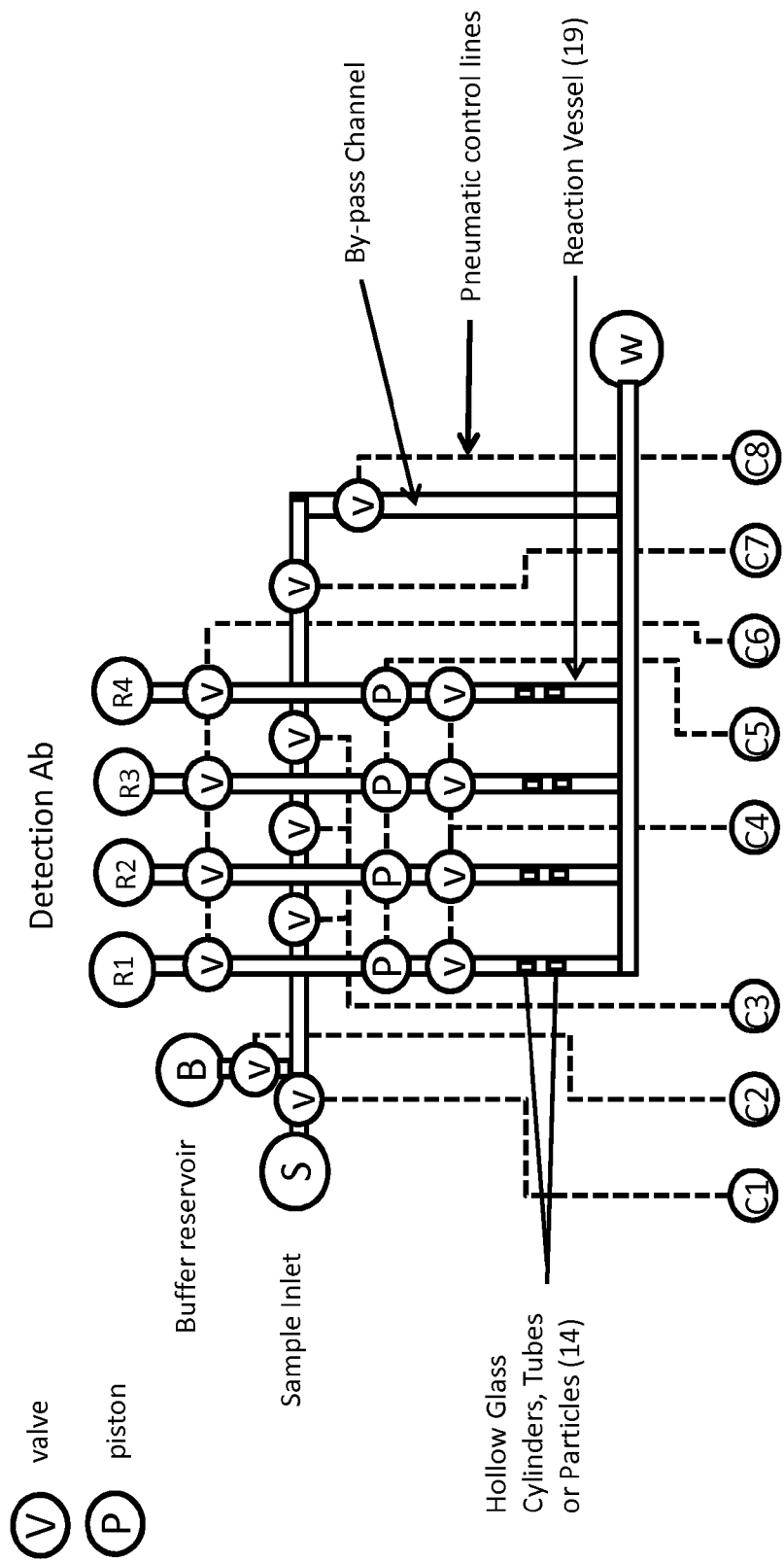
Fig. 6c: 4 plex architecture with common pump control, common waste reservoir and by-pass channel.

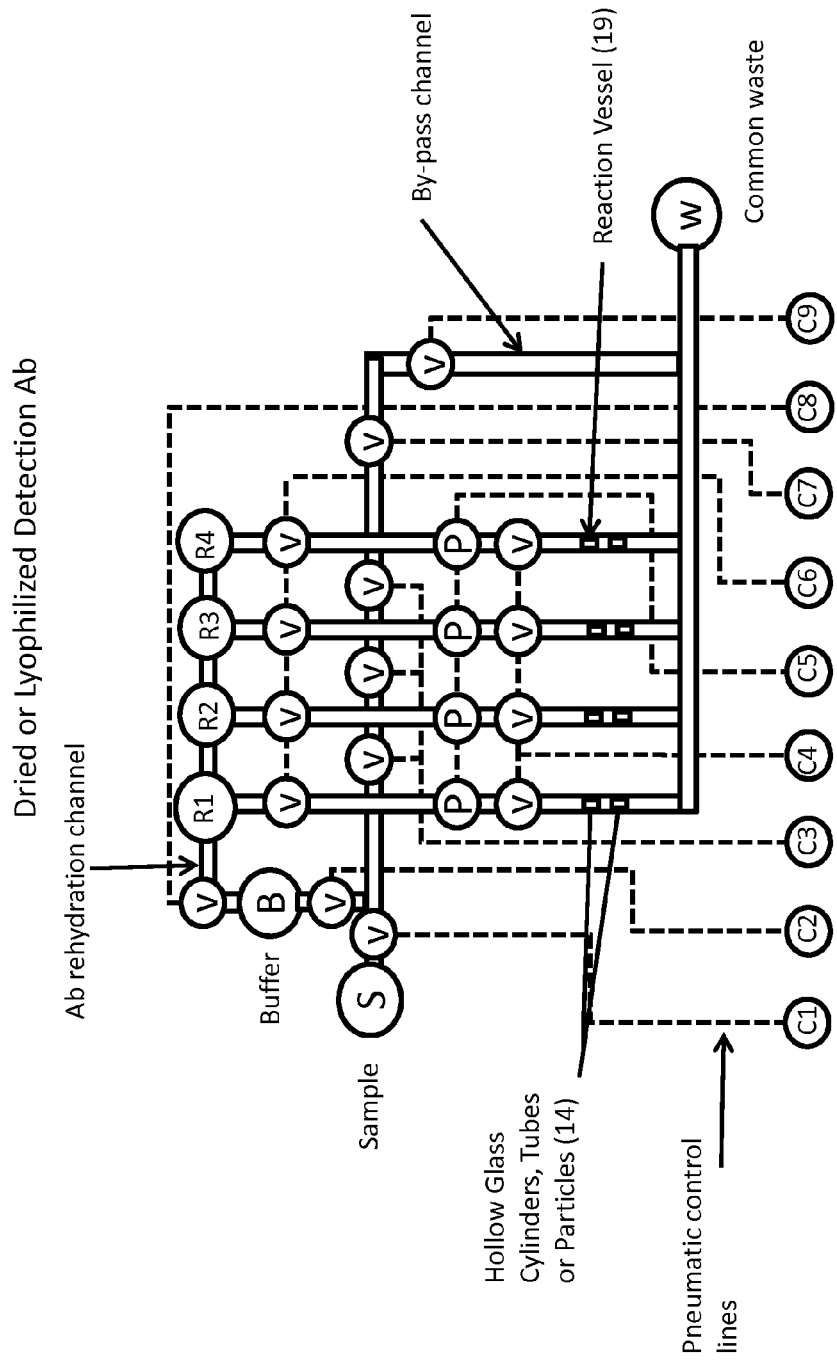
Fig. 6d: 4 plex architecture with common pump control, common waste reservoir, by-pass channel and antibody rehydration channel.

Fig. 7a: Prototype microfluidic sub unit

Fig. 7b: Magnified image of 3 reaction vessels embedded in isolation channel.

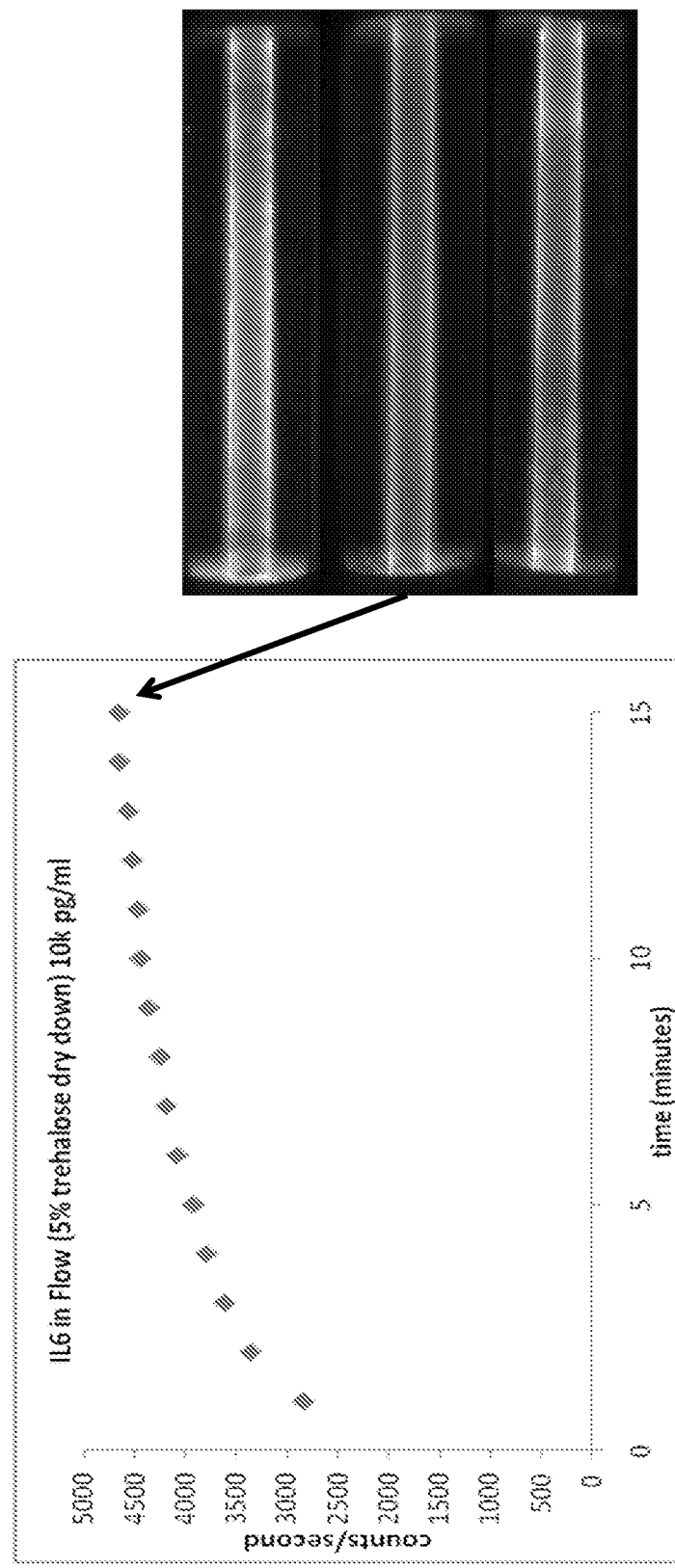
Fig. 7c (2)
Fig. 7c (1)

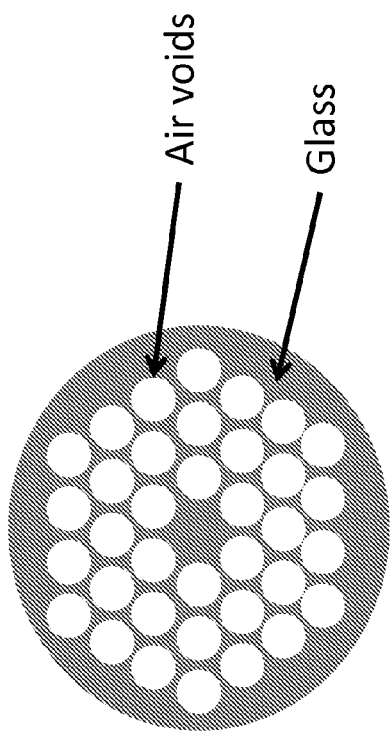
Fig. 8a
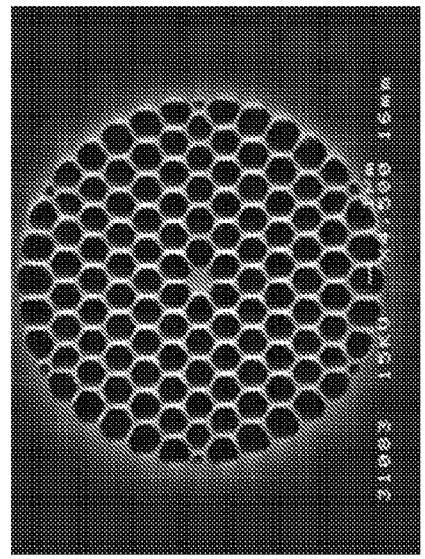
Fig. 8b
Figure 8

METHOD AND APPARATUS FOR PERFORMING ASSAYS

CROSS-REFERENCE TO RELATED APPLICATIONS

This application claims benefit to provisional patent application Ser. No. 61/263,572, filed 23 Nov. 2009, which is hereby incorporated by reference in its entirety.

BACKGROUND OF THE INVENTION

1. Field of the Invention

The present invention relates to a method and apparatus for performing assays; and more particularly relates to a method and apparatus for performing chemical, biological or biochemical assays using microfluidic technology.

2. Brief Description of Related Art

One of the primary factors affecting the data quality of a multiplexed system is biological cross reactivity, which is caused when multiple analytes and a multi-reagent detection cocktail are mixed in a single reaction vessel. For example, in a protein assay, the mixing of analytes (proteins) and the detection cocktail (labeled antibodies) can result in unintended secondary cross-reactions or interference that distort the measurements and severely compromise data quality. This biological cross reactivity can be mitigated by attempting to design the assay with components that do not negatively react; however, this becomes increasingly impractical and difficult (due to the high number of variables introduced) as the multiplex level increases. Moreover, even for sets of antibodies in the assay with components that do not negatively react, the multiplexed result is still typically relative to the performance of any one of the individual components, due to the application of a common assay buffer across all of the antibodies, which is typically not the optimal buffer with respect to pH, salinity, etc for each of the antibodies.

SUMMARY OF THE INVENTION

The present invention provides a new and unique method and apparatus for performing a chemical, biochemical, or biological assay on a sample, including a biological assay, e.g., on a patient sample, such as serum, plasma, cerebrospinal fluid, urine, blood, etc.

According to some embodiments of the present invention, the apparatus may take the form of an assay device or apparatus comprising: a microfluidic assay cartridge or device that contains at least one sample inlet well configured to receive a sample; and a microfluidic sub-unit associated with the microfluidic assay cartridge and comprising microfluidic channels, micro-valves and at least one separate and fluidicly isolated isolation channel, and at least one hollow element, e.g. including at least one hollow glass cylinder, tube or particle. The at least one hollow element may be functionalized with a capture moiety or molecules so as to form at least one reaction vessel. The microfluidic channels and micro-valves may be configured to respond to signaling containing information about performing the assay and to controllably receive the sample and at least one reagent in the at least one reaction vessel, and to provide from the at least one reaction vessel light containing information about the assay performed on the sample inside the at least one reaction vessel as a result of said at least one reagent.

By way of example, the microfluidic channels and micro-valves may also be configured to respond to the signaling containing information about performing the assay and to introduce into the at least one reaction vessel some combination of the following:

assay reagents, including a plurality of reagents, such as labeled antibodies, reagents, including an enzymatic substrate, for producing an emitted light signal, and introduce a wash solution to remove any non-specifically bound proteins or antibodies and/or hydrate dry reagents with a buffer;

where the at least one reaction vessel may be configured to allow chemical reactions to take place for performing the assay, and to provide emitted light containing information about the assay performed to be interrogated, based at least partly on the signalling received.

According to some embodiments, the present invention may comprise one or more of the following features: The microfluidic sub-unit may be configured to contain on-board the assay reagents, including the plurality of reagents, such as labeled antibodies, to contain on-board the reagents such as an enzymatic substrate for producing the emitted light signal, and/or on-board the wash solution to remove any non-specifically bound proteins or antibodies. These microfluidic sub units may also be configured such that the on-board reagents, such as those defined above, are contained in a dehydrated form, and are rehydrated by control signals to the microfluidic system that introduces buffer fluids to the said dehydrated reagents. Embodiments are also envisioned in which the assay reagents, the enzymatic substrate or wash solution are not contained on-board, but instead form part of another device, apparatus or equipment and provided to the assay device or apparatus. The apparatus may be configured with at least one common on-board waste receptacle or individual on-board waste receptacles that are configured to capture the wash solution, along with non-specifically bound proteins or antibodies. The microfluidic assay cartridge may be configured to be disposable. The apparatus may comprise a detection system configured to respond to the emitted light signal provided from at least one reaction vessel, and provide a signal containing information about the assay performed in relation to the at least one reaction vessel. The apparatus may comprise a controller configured to execute a computer program code and to provide the signaling to the microfluidic channels and micro-valves in order to perform the assay. Each of the series of microfluidic channels may be configured to correspond to a respective one of the at least one sample inlet well. Embodiments for some assays are also envisioned in which the wash is optional, and only the assay reagents and the enzymatic substrate are introduced, but not the wash. The at least one reaction vessel may be contained in a channel that may be configured to conduct independent assays, where the channel may be understood to be separate and fluidicly-isolated from other channels so as to substantially eliminate cross reactivity between the assays performed in the respective channels. The at least one reaction vessel contained in each isolation channel may be functionalized with the same capture moiety or capture molecules; or the at least one reaction vessel contained in each isolation channel may be each functionalized with a different capture moiety or capture molecules; or some combination thereof. The at least one hollow element may be configured as a honeycomb with multiple axial cavities or chambers. The at least one reagent may comprises a plurality of reagents.

According to some embodiments of the present invention, the apparatus may take the form of a controller that may be configured to control the performance of an assay by an assay device comprising a microfluidic assay cartridge that contains at least one sample inlet well configured to receive a sample; and a microfluidic sub-unit associated with the microfluidic assay cartridge and comprising microfluidic channels, micro-valves and at least one hollow element, the at least one hollow element being functionalized with a capture moiety or molecules so as to form at least one reaction vessel.

In this embodiment, the controller may comprise:

at least one processor and at least one memory device, including computer program code; the at least one memory device and the computer program code may be configured, with the at least one processor, to cause the controller at least to provide signalling containing information about performing the biological assay to the microfluidic channels and micro-valves, where the microfluidic channels and micro-valves are configured to respond to the signaling, to direct the sample from the at least one sample inlet well to the at least one reaction vessel, and to introduce into the at least one reaction vessel at least one reagent, so as to provide from the at least one reaction vessel light containing information about the assay performed on the sample inside the at least one reaction vessel as a result of the at least one reagent.

According to some embodiments, the present invention may also take the form of a method for performing the assay process using a new and unique separation technique consistent with that set forth above. The method may be implemented by providing the means set forth above for automatically separating components where negative cross reactions may occur, and by employing the microfluidic assay cartridge or device that will automate some of the manual steps typically associated with these types of tests. The separation technique set forth herein for performing the assay process will substantially minimize the need to design around cross reactivity. By way of example, the method may comprise some combination of the following:

- functionalizing at least one hollow element by chemically cross-linking or passively adhering a capture antibody specific for a target analyte of interest onto the surface of the hollow element;
- introducing a precise volume of a sample, which may contain a patient sample, including serum, plasma, cerebrospinal fluid, urine, blood, etc., by flowing the sample into a channel containing at least one reaction vessel, including either by positive or negative pressure, during which time the target analyte of interest is retained by virtue of specific binding to the capture antibody coated onto the surface of the at least one reaction vessel;
- rinsing the reaction vessel with a buffer solution to wash away the unbound target analytes (e.g., protein);
- either flowing a second antibody, referred to as a detection antibody based at least partly on the fact that the detection antibody is coupled to a fluorescent tag (conjugate) capable of emitting a light signal, whereupon the detection antibody binds to the target analyte retained on the surface of the at least one reaction vessel via the capture antibody, or alternatively flowing a second antibody without a fluorescent conjugate, rinsing the reaction vessel with a buffer to wash away unbound detection antibody, and then adding a fluorescent conjugate in a subsequent step;
- rinsing the reaction vessel with a buffer solution to remove any unbound fluorescent conjugate,
- irradiating a fluorescent chemical tag with an appropriate excitation wavelength onto the reaction vessel;
- detecting an amount of fluorescent light emitted by the tagged detection antibody as a result of irradiating; and
- quantifying an amount of the target analyte captured by the amount of fluorescent light emitted by the tagged detection antibody as a result of irradiating the fluorescent chemical tag with the appropriate excitation wavelength onto the reaction vessel, where the amount of analyte on the surface of reaction vessel will be proportional to the amount of light emitted by the fluorescently labeled detection antibody, and hence is directly proportional to the amount of analyte within the patient sample.

According to some embodiments, the present invention may also take the form of an apparatus consistent with that described above, but where the microfluidic channels are configured to respond to a control impulse containing information about performing the assay and to receive the sample and at least one reagent in the reaction vessel. By way of example, the control impulse may take the form of at least one control signal that causes pneumatic control lines to open or close micro-valves arranged in relation to the microchannel that causes the sample and the at least one reagent to flow into the at least one reaction vessel in order to perform the assay; or alternatively that causes a device arranged in relation to the microchannel to provide positive or negative pressure in the microchannel that causes the sample and the at least one reagent to flow into the at least one reaction vessel in order to perform the assay.

Embodiments are also envisioned within the spirit of the present invention in which, instead of using at least one hollow element having a capture moiety or molecules, one may use encoded or non-encoded microparticles having an outside surface functionalized, e.g. by coating, with the capture moiety or molecules, consistent with that disclosed in Ser. No. 12/945,459, filed 12 Nov. 2010, which is hereby incorporated by reference in its entirety.

Advantages

The present invention employs a novel reaction vessel that, in and of itself, enables very low cost manufacturing, fast reaction time, low sample volume, high sensitivity, and large dynamic range. The novel hollow reaction vessel may take the form of the at least one hollow element that has been functionalized with the capture moiety or capture molecules.

Advantages of embodiments of the present invention include substantially minimizing the need to design around cross reactivity by providing a means for automatically separating components where negative cross reactions occur. Additionally, this assay device will improve ease of use by employing a disposable microfluidic assay cartridge that will automate some of the manual steps typically associated with these types of tests. This assay device will optimize buffer conditions to produce independently optimized assays. The optimized buffer conditions may include optimizing in relation to the pH, salinity or both. This assay device will also allow samples to be independently diluted with buffer solution with respect to each channel.

It is the purpose of the present invention to deliver an apparatus or a method that provides multi-sample, multiplex assays with data quality that is significantly improved over current methods while at the same time providing greater ease of use.

BRIEF DESCRIPTION OF THE DRAWING

The drawing, which are not necessarily drawn to scale, includes the following Figures:

FIGS. 1(a) which shows a microfluidic assay cartridge or device according to some embodiments of the present invention; FIG. 1(b) which shows a microfluidic sub-unit corresponding to at least one sample inlet well of the microfluidic cartridge shown in FIG. 1(a) according to some embodiments of the present invention; and FIG. 1(c) which shows a flowchart having steps for performing a biological assay, e.g., using the combination of the microfluidic assay cartridge or device shown in FIG. 1(a) and the microfluidic sub-unit shown in FIG. 1(b).

FIG. 2 is a diagram showing detail of an isolation channel with embedded reaction vessel that forms part of the microfluidic sub-unit shown in FIG. 1(b) according to some embodiments of the present invention.

FIG. 3 shows channel geometry of an isolation channel that can form part of the microfluidic sub-unit shown in FIG. 1(b) according to some embodiments of the present invention, including FIG. 3a showing a magnified photograph of examples of square channels, a partially filled channel and a pneumatic channel; FIG. 3b showing an example of a channel having no fill; FIG. 3c showing an example of a channel having 20% fill; FIG. 3d showing an example of a channel having 60% fill; FIG. 3e(1) showing a diagram of a hollow element fit within walls of the isolation channel looking from the top; FIG. 3e(2) showing a diagram of the hollow element fit within walls of the isolation channel shown in FIG. 3e(1) looking from the end along the longitudinal axis of the hollow element; FIG. 3f(1) showing a diagram of a hollow element fit within walls of the isolation channel with fill material looking from the top; FIG. 3f(2) showing a diagram of the hollow element fit within walls of the isolation channel with fill shown in FIG. 3f(1) looking from the end along the longitudinal axis of the hollow element; and FIG. 3g is an epoxy down select matrix showing rows of epoxy in relation to columns of parameters, including indication of type, viscosity, dispensable, fluorescence, cure method, comment and acceptable.

FIG. 4 shows a magnified photograph of an example of a pneumatically actuated pump having valves, a piston, a fluidic channel and pneumatic lines according to some embodiments of the present invention.

FIG. 5 shows an example of pump operation in relation to valves and a piston arranged between an inlet reservoir and a destination according to some embodiments of the present invention.

FIG. 6a(1) shows an example of a 4-plex architecture with independent pump control and individual waste reservoirs according to some embodiments of the present invention; FIG. 6a(2) shows an example of Normally Closed (NC) (vacuum actuated) states for buffer pumping (1 complete cycle) for the 4-plex architecture shown in FIG. 6a(1) according to some embodiments of the present invention; FIG. 6b shows an example of a 4-plex architecture with independent pump control and a common waste reservoir according to some embodiments of the present invention; FIG. 6c shows an example of a 4-plex architecture with a common pump control, a common waste reservoir and a by-pass channel according to some embodiments of the present invention; and FIG. 6d shows an example of a 4-plex architecture with a common pump control, a common waste reservoir, a by-pass channel and an antibody rehydration channel according to some embodiments of the present invention.

FIG. 7a is a photograph of a microfluidic chip according to some embodiments of the present invention; FIG. 7b shows an expanded and magnified view of three reaction vessels embedded in an isolation channel of the microfluidic chip shown in FIG. 7a according to some embodiments of the present invention; FIG. 7c(1) is a graph of counts per second versus time of a real time signal evolution due to binding of a secondary Ab (IL6) to a captured antigen inside three embedded reaction vessels; FIG. 7c(2) shows fluorescence images of three embedded reaction vessels after 15 minutes.

FIG. 8 includes the following: FIG. 8a which is a view of a hollow element having a hex-shaped honeycomb configuration with multiple reaction cavities or chambers according to some embodiments of the present invention, and FIG. 8b is a view of a hollow element having a circularly-shaped honeycomb configuration with multiple reaction cavities or chambers according to some embodiments of the present invention.

DETAILED DESCRIPTION OF THE INVENTION

FIG. 1

Figure 1:
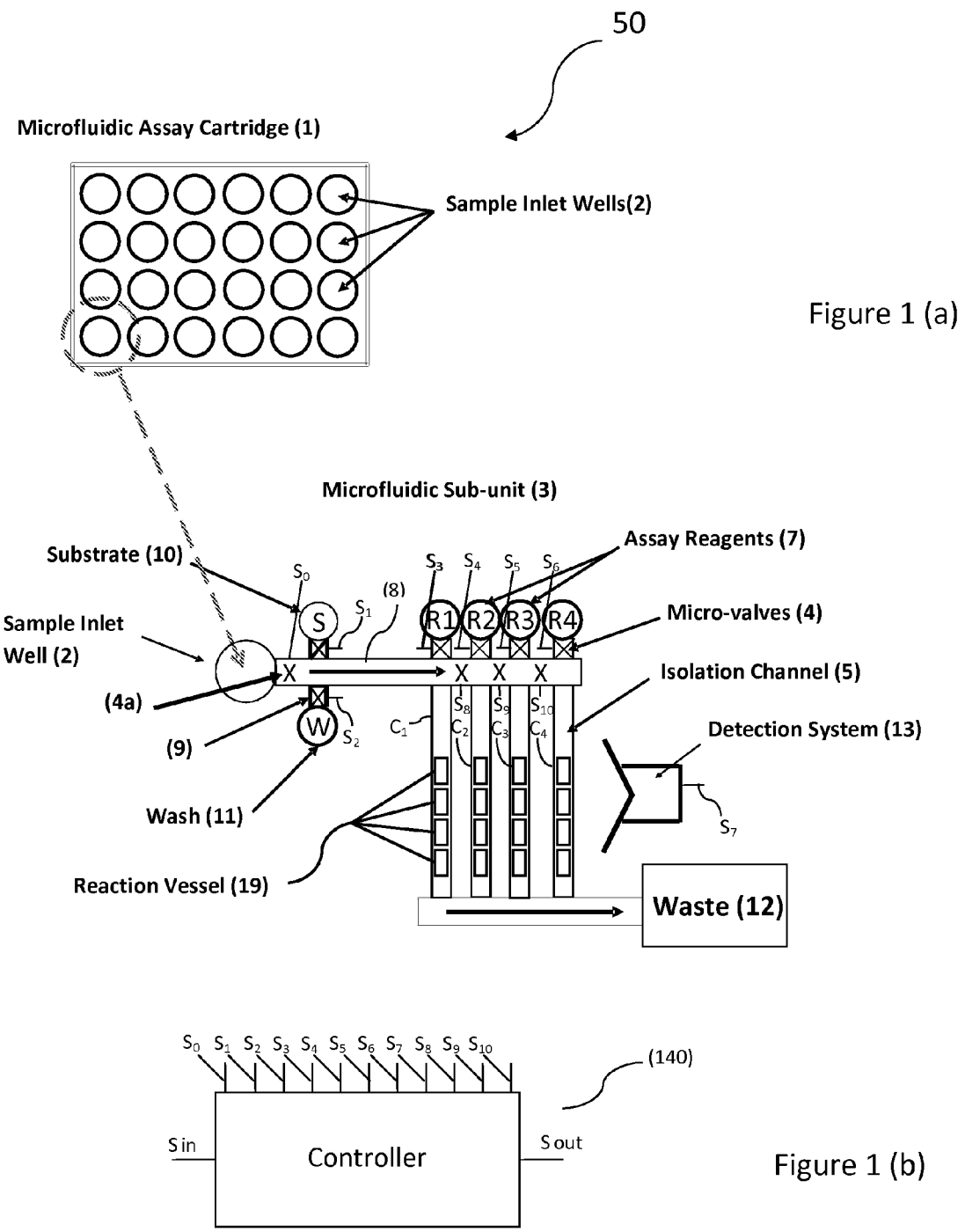
FIG. 1 includes the following.

In FIG. 1, the present invention takes the form of an apparatus generally indicated as 50 shown in FIG. 1 that may include a microfluidic assay cartridge or device (1) which will contain at least one sample inlet well (2), as shown in FIG. 1(a). Each sample inlet well (2) will feed, e.g. based at least partly on some control logic, into a respective microfluidic sub-unit (3) embedded within the microfluidic assay cartridge or device (1), as shown in FIGS. 1 and 1(b). In FIG. 1(a), the microfluidic assay cartridge or device (1) is shown by way of example as having a plurality of sample inlet wells (2) in the form of 4 by 6 matrix, totally 24 sample inlet wells. The scope of the invention is not intended to be limited to the number of sample inlet wells (2), and is intended to include any number of sample inlet wells (2) ranging from 1 sample inlet well (2) to N sample inlet wells (2). The microfluidic assay cartridge or device (1) and/or microfluidic sub-unit (3) may be constructed and/or made from a material so as to be disposable or reusable, and the scope of the invention is not intended to be limited to the type or kind of material used to construct or make the microfluidic assay cartridge or device (1) and/or microfluidic sub-unit (3) either now known or later developed in the future.

The microfluidic sub-unit (3) contains a series of microfluidic channels and micro-valves (4) that direct a sample, including a patient sample, such as serum, plasma, cerebrospinal fluid, urine, blood, etc., from the at least one sample inlet well (2) to separate and fluidicly-isolated channels (5) that contain one or more reaction vessels (19), which have been functionalized with a capture moiety or capture molecules such as antibodies, antigens, or oligomers, as shown in FIG. 1(b). In FIG. 1b, each isolation channel (5) is shown having four reaction vessels (19) for a combine total of 16 reaction vessels is channels C1, C2, C3, C4, although the scope of the invention is not intended to be limited to any particular number of reaction vessels (19) in each isolation channel (5), consistent with that described herein. Assay reagents (7) including reagents R1, R2, R3, R4, such as labeled antibodies, will be introduced into the separate isolation channels (5) via the microfluidic channels (8) and micro-valves (4). Additionally, the microfluidic channels (8) and micro-valves (9) are provided to introduce reagents such as an enzymatic substrate (10) for producing an emitted light signal and a wash solution (11) to remove any non-specifically bound proteins or antibodies. The wash solution (11), along with non-specifically bound proteins or antibodies, is captured in an on-board waste receptacle (12). Chemical reactions taking place in the reaction vessels (19) are interrogated by a detection system (13). (It is noted that the addition of the enzymatic substrate (10) forms part of one technique of performing the biological assay, which may be contrasted to an alternative technique described below in relation to FIG. 6. See also the alternative embodiments described in relation to FIG. 1(c).)

FIG. 2 shows in further detail as generally indicated by (6) the isolation channel (5) and reaction vessel (19) embedded therein which has been designed such that it can tolerate a large confocal region or zone (18), and as a consequence may not require high resolution optics to avoid background fluorescence. In addition, the isolation channel and reaction vessel have been designed to enable very low cost manufacturing, and may include leveraging existing fiber optic and injection molded plastic technology. This low cost is achieved while at the same time providing very good optical qualities, increased sensitivity, decreased reaction time, large dynamic range, and low sample volume requirements.

The biological reactions take place inside at least one hollow element (14) which has been functionalized with a capture moiety or molecules (15), so as to form the reaction vessel (19). By way of example, the at least one hollow element (14) may be configured or fabricated by drawing glass tubing with an outer diameter and an inner diameter, and cutting or dicing it, e.g., with a dicing saw. The at least one hollow element (14) may also be configured or fabricated by etching out the core of commercially available high NA fused silica optical fibers or rods, which provide extremely high optical quality at a very low cost. The present invention is described by way of example with the at least one hollow element (14) being made of glass; however, the scope of the invention is intended to include making the at least one hollow element (14) from other types or kind of material either now known or later developed in the future, including other types or kinds of non-glass materials. The at least one hollow element (14) may be suspended in a housing (16) with a significant amount of air space (17) surrounding the outside diameter of the at least one hollow element (14). This air space (17) provides the large confocal zone (18) by providing an area that is free from any introduced background fluorescence. The at least one hollow element (14) may be installed with a press or friction fit into and received by walls of the housing (16), which is described in further detail below, that will direct the sample through the inside diameter of the at least one hollow element (14), and prevent the sample from entering the air space (17) surrounding the at least one hollow element (14). The at least one hollow element (14) may be configured or designed with a cavity or chamber having a very small inside diameter (e.g., approximately 10 µm inner diameter (ID)) and a length-to-I.D. aspect ratio of, e.g., approximately 20:1 (approximately 200 µm L). This configuration provides the reaction vessel (19) with a very high surface area-to-volume ratio, which in-turn drives fast reaction kinetics. In addition, the effect of the sample being forced through a very low volume reaction vessel increases the probability of a binding event because a higher proportion of the sample comes in contact with the functionalized surface of the hollow element, thereby increasing sensitivity. In FIG. 2, the isolation channel and reaction vessel detail is understood to take the form of at least one hollow element (14) that is functionalized with the capture moiety or molecules (15), and is arranged in and coupled to the housing (16) in an isolation channel (5) as shown.

As shown in FIG. 2, light $L_{in}$ from a light source (20) can be passed through a dichroic beam splitter (22), a lens (24) and the air space (17) to the large confocal region or zone (18); and light $L_{out}$ can be passed back through the air space (17), the lens (24), the dichroic beam splitter (22), a lens (26) to the detector (13).

In an alternate embodiment of this invention, a plurality of hollow elements (14) of decreasing inside diameters can be functionalized and placed in-line to address varying analyte densities, prevent oversaturation, and extend the dynamic range of the systems analysis capabilities. Alternatively, a plurality of hollow elements of the same diameter that have been functionalized with different loading densities of the capture moiety or molecules can be placed in-line to address varying analyte densities, prevent over saturation, and extend the dynamic range. It is also envisioned that combinations of the above configuration can be employed to achieve optimized results.

The scope of the invention is not intended to be limited to any particular type or kind of sample that forms part of the assay process, and is intended to include samples of substance both now known and later developed in the future.

The at Least One Sample Inlet Well (2)

In FIG. 1, each of the at least one sample inlet well (2) of the disposable microfluidic assay cartridge or device (1) corresponds to a respective microfluidic sub-unit (3) embedded within the disposable microfluidic assay cartridge (1). However, the scope of the invention is also intended to include embodiments in which multiple sample inlet wells (2) of the disposable microfluidic assay cartridge or device (1) are configured to correspond to a respective microfluidic sub-unit (3) via, e.g., a manifold device (not shown).

The Assay Reagents and Channel

In FIG. 1, each assay reagent R1, R2, R3, R4 may correspond to, feed into and be assigned to a respective isolation channel C1, C2, C3, C4. However, the scope of the invention is also intended to include embodiments in which each assay reagent R1, R2, R3, R4 feeds into multiple channels C1, C2, C3, C4.

The Detection System (13)

In FIG. 1, each of the microfluidic sub-units (3) embedded within the disposable microfluidic assay cartridge (1) has a respective detection system (13). However, the scope of the invention is also intended to include embodiments in which multiple microfluidic sub-unit (3) are configured to correspond to a respective detection system (13). By way of example, a first column or group of four microfluidic sub-unit (3) may correspond to a first detection system (13); a second column or group of four microfluidic sub-unit (3) may correspond to a second detection system (13); . . . ; and a sixth column or group of four microfluidic sub-unit (3) may correspond to a sixth detection system (13). Alternatively, by way of example, a first row or group of six microfluidic sub-unit (3) may correspond to a first detection system (13); a second row or group of six microfluidic sub-unit (3) may correspond to a second detection system (13); . . . ; and a fourth row or group of six microfluidic sub-unit (3) may correspond to a fourth detection system (13). The scope of the invention is also intended to include embodiments in which N microfluidic sub-unit (3), where N, e.g., equals 24 corresponding to that shown in FIG. 1, are configured to correspond to a single detection system (13). The scope of the invention is also intended to include embodiments in which the detection system (13) is on-board and forms part of microfluidic sub-unit (3), as well as embodiments where the detection system (13)

is not on-board but forms part of another device, apparatus or equipment either now known or later developed in the future.

The Controller (140)

The apparatus may also include a controller (140) for implementing the functionality associated with the assay performed by the microfluidic sub-unit (3) embedded within the disposable microfluidic assay cartridge or device (1). The controller (140) may be configured to execute a computer program code and to provide the signaling along signal paths, e.g., $S_0, S_1, S_2, S_3, S_4, S_5, S_6, \ldots, S_{10}$ to each microfluidic channel (8) and/or micro-valves (4, 9) in order to perform the assay. In operation, the controller (140) may be configured to execute the computer program code and to exchange signaling along signal path $S_7$ with the detection system (13), including receiving a detection system signal containing information about the reactions taking place in the reaction vessels (19) being interrogated by the detection system (13). The controller (140) may also be configured to receive an input signal(s) along signal path $S_{in}$, and to provide an output signal(s) along signal path $S_{out}$. By way of example, the output signal along signal path $S_{out}$ may contain either the raw detection system signal containing information about the reactions taking place in the reaction vessels (19) being interrogated by the detection system (13), or a processed detection system signal containing information about the reactions taking place in the reaction vessels (19) being interrogated by the detection system (13). By way of example, the input signal along signal path $S_{in}$ may contain information to control or modify the functionality of the controller (140), including a signal requesting the provisioning of the output signal along signal path $S_{out}$. The scope of the invention is not intended to be limited to the type or kind of information being provided to or received by the controller (140) via the input signal along signal path $S_{in}$ or the type or kind of information being provided from the controller (140) via the output signal along signal path $S_{out}$ either now known or later developed in the future. Further, by way of example, the controller (140) may be implemented using hardware, software, firmware, or a combination thereof. In a typical software implementation, the controller (140) would include one or more microprocessor-based architectures having a processor or microprocessor, memory such as a random access memory (RAM) and/or a read only memory (ROM), input/output devices and control, data and address buses connecting the same. A person skilled in the art would be able to program such a microcontroller or microprocessor-based implementation with the computer program code to perform the functionality described herein without undue experimentation. The scope of the invention is not intended to be limited to any particular microprocessor-based architecture implementation using technology either now known or later developed in the future.

Embodiments are envisioned in which the controller (140) either is on-board and forms part of the apparatus (50), or is not on-board but forms part of another apparatus, device, system or equipment that cooperates with the apparatus (50) in relation to implementing the assay process with the microfluidic technology disclosed herein.

In FIG. 1(b), the microfluidic sub-unit (3) is shown, by way of example, with micro-valves (4, 9) arranged in relation to the substrate (10), the wash (11) and the assay reagents (7) to control the introduction of the assay reagents to the isolation channels (5) in response to the signalling along signalling paths $S_0, S_1, S_2, S_3, S_4, S_5, S_6, \ldots, S_{10}$ using steps 3-8 described below and set forth in the flowchart shown in FIG. 1(c). Embodiments are also envisioned in which the micro-valves (4) provide information back to the controller (140) via corresponding signalling along signalling paths $S_0, S_1, S_2, S_3, S_4, S_5, S_6, \ldots, S_{10}$, for controlling the introduction of the assay reagents (7), the substrate (10) and the wash (11). Embodiments are also envisioned in which other micro-valves are arranged at other points in relation to each microfluidic channel (8), e.g. such as micro-valves (4a) in FIG. 1(b) arranged in relation to the interface between each microfluidic channel (8) and the at least one sample inlet well (2) for controlling the provisioning of the sample into the microfluidic channel (8) with signalling along signal path $S_0$. Embodiments are also envisioned in which other micro-valves are arranged in relation to the isolation channels (5), including at either or both ends, so as to control the passage of the solution, reagents or buffer through the isolation channels (5). The scope of the invention is not intended to be limited to the number, position, or arrangements of the micro-valves, like (4) or (4a) or (9).

By way of example, the micro-valves (4, 4a, 9), isolation channels (5), detection system (13), along with other components or devices shown and described herein in relation to FIG. 1, are either known in the art, or can be implemented to perform the desired functionality without undue experimentation by one skilled in the art; and the scope of the invention is not intended to be limited to any particular type or kind thereof either now known or later developed in the future. Furthermore, based of the disclosure herein, one skilled in the art could implement the apparatus 50 shown in FIG. 1, including the microfluidic assay cartridge (1) shown in FIG. 1(a) and the microfluidic sub-unit (3) embedded therein shown in FIG. 1(b), to perform the desired functionality without undue experimentation.

The present invention is described by way of using micro-valves configured to control the flow of one or more of the sample, the assay reagents (7), the substrate (10) and the wash (13) into the at least one separate and fluidicly-isolated isolation channels (5). However, the scope of the invention is intended to include using other types or kind of techniques either now known or later developed in the future to control the flow of one or more of the sample, the assay reagents (7), the substrate (10) and the wash (13) into the at least one separate and fluidicly-isolated isolation channels (5), e.g., such as by using a configuration to provide positive pressure to push and cause the flow of one or more of the sample, the assay reagents (7), the substrate (10) and the wash (13) into the at least one separate and fluidicly-isolated isolation channels (5), or such as by using a configuration to provide negative pressure (e.g. a vacuum) to pull (or draw) and cause the flow of one or more of the sample, the assay reagents (7), the substrate (10) and the wash (13) into the at least one separate and fluidicly-isolated isolation channels (5), or such as by using some combination of pushing and/or pulling to cause the flow of one or more of the sample, the assay reagents (7), the substrate (10) and the wash (13) into the at least one separate and fluidicly-isolated isolation channels (5). The configuration to provide positive pressure may be configured on the upper end (as shown in FIG. 1(b)) of the at least one separate and fluidicly-isolated isolation channels (5) in relation to the assay reagents (7) and channels C1, C2, C3, C4, while the configuration to provide negative pressure may be configured on the lower end (as shown in FIG. 1(b)) of the at least one separate and fluidicly-isolated isolation channel (5) in relation to the waste (12) and channels C1, C2, C3, C4.

Immunoassay Process for Sandwich ELISAs

By way of example, the process of conducting an immunoassay in a cartridge according to the present invention using a sandwich enzyme-linked immunosorbent assay (ELISA) may entail some combination of the following:

Step 1: A capture antibody specific for the target analyte of interest is chemically cross-linked onto the surface of the hollow element (14) in FIG. 2 so as to form the reaction vessel (19)).

Step 2: The reaction vessel (19) once placed into the isolation channel (5) is then ready to receive the patient sample (serum, plasma, cerebrospinal fluid, urine, blood, etc).

Step 3: A precise volume of the patient sample is then introduced by flowing the material into the reaction vessel (19), either, e.g., by positive or negative pressure, during which time the target analyte of interest is retained by virtue of specific binding to the capture antibody coated onto the interior surface of the reaction vessel (19).

Step 4: The reaction vessel (19) is then rinsed with a buffer to wash away the unbound protein.

Step 5: The second antibody, referred to as a detection antibody since it is coupled to a fluorescent tag capable of emitting a light signal, is then is flowed into the reaction vessel (19) whereupon it binds to the target analyte retained on the interior surface via the capture antibody.

Step 5a: An alternative embodiment of this process may be to use a second antibody without a fluorescent conjugate, and then to add the fluorescent conjugate in a subsequent step. Note that this may also include an additional rinse step prior to adding the fluorescent conjugate.

Step 6: The reaction vessel (19) is then rinsed again with a buffer to remove unbound protein, and the excess fluorescent tag.

Step 7: The amount of the target analyte captured is then quantified by the amount of fluorescent light emitted by the detection antibody as a result of irradiating the fluorescent chemical tag with the appropriate excitation wavelength onto the reaction vessel (19).

Step 8: The amount of analyte within the reaction vessel (19) is proportional to the amount of light emitted by the detection antibody fluorescent tag, and hence is directly proportional to the amount of analyte within the patient sample.

The controller (140) shown in FIG. 1(b) may be implemented and configured to provide the signalling to perform the biological assay using, e.g., steps 3-8 set forth above.

The scope of the invention is described by way of example using the sandwich ELISA biological assay technique. However, the scope of the invention is not intended to be limited to using the sandwich ELISA biological assay technique, e.g., embodiments are also envisioned using other types or kind of biological assay techniques either now known or later developed in the future, including an "indirect" ELISA, a competitive ELISA, a reverse ELISA, as well as other non-ELISA techniques.

FIG. 3: Channel Geometry

By way of example, FIG. 3 shows channel geometry of an isolation channel (5) that may form part of the microfluidic sub-unit (3) shown in FIG. 1(b) according to some embodiments of the present invention.

FIG. 3a shows examples of a square channel, a partially filled channel and a pneumatic channel.

In some embodiments, the channel may be partially filled with Polydimethylsiloxane (PDMS) fillet to form a conformal surface for a membrane seal, configured to engage an outer surface of the hollow element (14). See FIG. 3c. By way of example, partially filling a channel with PDMS could be used to engage the outer surface of the hollow element so as to reduce the free volume around the cylinder.

If no fill (square channel) is used, then the channel cannot be closed by the membrane, which may take the form of a very thin layer of PDMS. See FIG. 3b, where air pressure, e.g. from the pneumatic control of a microvalve, can partially push the membrane down into the channel, but can still result in a fluidic leak path, as shown.

Alternatively, the use of a higher degree of fill reduces strain on the membrane, lowers required air pressure, but creates channel occlusion.

PDMS is a material that belongs to a group of polymeric organosilicon compounds that are commonly referred to as silicones. PDMS material doesn't fluoresce which is important in processing the light signal received back from the reaction vessel (19).

FIGS. 3e(1) and 3e(2) show the hollow element (14) fit within walls W1, W2 of the housing (16) that forms part of the isolation channel (5). See FIG. 1b and FIG. 3b. The hollow element (14) is retained in channel by friction fit with walls W1, W2. Free space exists between outside of the hollow element (14) and channel walls W1, W2.

FIGS. 3f(1) and 3(f)2 show the hollow element (14) fit within walls W1, W2 of the housing (16) that forms part of the isolation channel (5) with fill. See FIG. 1b and FIGS. 3b and 3c. The hollow element (14) is retained in channel (5) by a fill material that may take the form of an epoxy-like material, silicone rubber, etc., placed in channel floor prior to insertion of the hollow element fit (14). Alternatively, the isolation channel (5) may be completely filled around the hollow element fit (14) to completely block flow around particle.

In FIG. 3g, an epoxy down select matrix shows rows of epoxy in relation to columns of parameters, including indication of type, viscosity, dispensable, background fluorescence, cure method, comment and acceptable. The PDMS material includes the Sylgard 184, Sylgard 186 and the Nusil materials listed.

FIG. 4: Pneumatically Activated Pump

FIG. 4 shows, by way of example, one prototype of a pneumatically actuated pump having valves, a piston, a fluidic channel and pneumatic lines according to some embodiments of the present invention. In FIG. 4, the piston displacement for this prototype is about 200 nl (nanoliters), which may be far more than what is likely to be required.

FIG. 5: Pump Operation

FIG. 5 shows an example of pump operation in relation to valves and a piston arranged between an inlet reservoir and a destination according to some embodiments of the present invention. In FIG. 5, the pump operation includes pumping that is accomplished by combining 2 pneumatically actuated valves V1, V2 with at least one pneumatically actuated piston located between the two valves V1, V2. The purpose of the piston is simply to displace fluid, either by pulling it in from a reservoir or pushing it in the direction of the flow. The valves V1, V2, which buttress the piston, ensure unidirectional flow. Full operation is accomplished by actuating the 3 components in a particular sequence. For example, to move fluid from the inlet reservoir to the destination, as shown in FIG. 5, a valve sequence may entail the following: close the valve V1, compress the Piston, close the valve V2, open the valve V1, decompress the piston, close valve V1, open the valve V2 and compress the Piston. In a larger network of channels and valves, the flow can be generated by combining any set of 2 valves and a piston. In other words, valves can be used as simple open and close valves or they can be incorporated into a pump as described here.

FIG. 6: Various 4-plex Architectures

By way of example, FIGS. 6a(1), 6b, 6c and 6d show various 4-plex architectures for performing an assay according to some embodiments of the present invention. For instance, FIG. 6a(1) shows a 4-plex architecture with independent pump control and individual waste reservoirs, and FIG. 6a(2) shows the NC (vac actuated) states for buffer pumping (1 complete cycle) for the 4-plex architecture shown in FIG. 6a(1), according to some embodiments of the present invention. In the fluidic network shown in FIG. 6a(1), there are a number of fluidic channels C1, C2, C3, C4 with pneumatically actuated valves V located at various locations along the channels. The valves V connected to one another are actuated simultaneously. Valve set 3 is pistons and valve set 4 is the outlet valves and these are used for all of the pumping operations regardless of the fluid source. Depending on which fluid is being pumped (sample, buffer or detection Ab) the particular valve used in combination to provide pumping may be 1, 8 or 7 respectively. FIG. 6a(2) shown the state diagram for one complete sequence required to pump buffer from the source through the main channels and out the their respective waste reservoirs.

By way of example, FIG. 6b shows a 4-plex architecture with independent pump control similar to the 4-plex in FIG. 6a(1), but with a common waste reservoir W feeding from the isolation channels (5).

By way of example, FIG. 6c shows an example of a 4-plex architecture with a common pump control and a common waste reservoir similar to the 4-plex in FIG. 6b, but with a by-pass channel feeding from the microchannel to the common waste reservoir.

By way of example, FIG. 6d shows an example of a 4-plex architecture with a common pump control, a common waste reservoir and a by-pass channel similar to the 4-plex in FIG. 6c, but with an antibody rehydration channel.

Method for Performing an Assay Using a Separation Technique

The present invention may also take the form of a method for performing the assay process using a new and unique separation technique consistent with that set forth above. The method may be implemented by providing the means set forth above for automatically separating components where negative cross reactions occur, and by employing the disposable microfluidic assay cartridge that will automate some of the manual steps typically associated with these types of tests. The separation technique set forth herein for performing the assay process will eliminate the need to design around cross reactivity.

By way of example, the method for performing an assay may be implemented using the microfluidic technology in FIG. 1 as follows:
providing a microfluidic assay cartridge (1) that contains at least one sample inlet well (2) configured to receive a sample; and a microfluidic sub-unit (3) associated with the microfluidic assay cartridge (1) and configured to controllably receive the sample from the microfluidic assay cartridge (1); the microfluidic sub-unit (3) comprising microfluidic channels (8), micro-valves (4, 4a, 9), and at least one separate and fluidicly isolated isolation channel (5), and at least one reaction vessel (19), the reaction vessel (19)) comprising at least one hollow element (14) which has been functionalized with a capture moiety or capture molecules (15);
responding to signaling containing information about performing the assay with the microfluidic channels (8) and micro-valves (4, 9), and controllably receiving the sample and the at least one reagent in the at least one reaction vessel (19), so as to provide light containing information about the assay performed on the sample inside the at least one hollow element (14) as a result of the at least one reagent.

The method may also comprise responding to the signaling containing information about performing the assay with the microfluidic channels (8) and micro-valves (4, 9) and introducing into the reaction vessel (19) the following:
assay reagents (7), including a plurality of reagents (R1, R2, R3, R4), such as labeled antibodies,
reagents, including an enzymatic substrate (10), for producing an emitted signal, and
a wash solution (11) to remove any non-specifically bound proteins or antibodies; and
allowing with the at least one reaction vessel (19) chemical reactions to take place for performing the assay, and providing the emitted light containing information about the assay performed to be interrogated, e.g. by the detection system (13).

Further, by way of example, the method for performing an assay may also be implemented using the microfluidic technology in FIG. 2.

Furthermore, by way of example, the method for performing a biological assay may also be implemented using the steps set forth above, including those set forth in relation to FIG. 1(c).

The Assay

Many different types and kinds of assays may be performed using the present invention, including a chemical assay or a biological assay.

For example, a singular and multiplexed biological assay may be performed by using at least one functionalized hollow glass cylinder, tube or particle (14) in different isolation channel (5), by using multiple functionalized hollow glass cylinders, tubes or particles (14) in the same isolation channel (5), or by using multiple functionalized hollow glass cylinders, tubes or particles (14) in multiple isolation channels (5).

Further, a multiplexed biological assay may be performed by using multiple reaction vessels, each with different concentrations of capture molecules, all located in a single isolation channel. For example, a first isolation channel C1 may include three reaction vessels, one with a low concentration of capture molecules immobilized on it, a second reaction vessel with a higher concentration of capture molecules immobilized on it, and third reaction vessel with an even higher concentration of capture molecules immobilized on it. A second isolation channel could include reaction vessels with the same range of capture concentrations or a completely different range of capture concentrations or a set of reaction vessels with all of the same reaction concentration. Further, a multiplexed biological assay may be performed by using multiple reaction vessels, each with different inner diameters, all located in the same isolation channel. For example, a first isolation channel C1 may include three reaction vessels, one with a small inside diameter and surface area, a second reaction vessel with a larger inside diameter and surface area, and third reaction vessel with an even larger inside diameter and surface area, so as to introduce different reaction kinetics. A second isolation channel C2 could contain the same set of reaction vessels with the same range of inner diameters or contain a completely different set of reaction vessels with a different range of inner diameters or with all of the same diameters.

Further still, a multiplexed biological assay may be performed by using positive and negative controls. For example, a first isolation channel C1 may include using a positive control, and a negative control while a second isolation channel C2 may also include using a positive and negative control that shouldn't react. Besides, biological assays with +/− controls may include using functionalized hollow glass cylinders, tubes or particles (14) having different antibodies, where the + control spikes and the − control does not react, but can be used, e.g., to gain information about background fluorescents.

Further still, a multiplexed biological assay may be performed by using different channels having different numbers of analytes, e.g., a first isolation channel C1 may include a first number of analytes (e.g. 1), a second isolation channel C2 may include a second number of analytes (e.g. 3), and a third isolation channel C3 may include a third number of analytes, . . . , an Nth isolation channel has an Nth number of analytes.

Further still, a multiplexed biological assay may be performed by using different isolation channels having different biological assays. For example, a first isolation channel C1 may include a first biological assay A, a second isolation channel C2 may include a second biological assay B, and a third isolation channel C3 may include a third biological assay A+B, so that channels can be looked at individually and together, which the channel B biological assay and the channel A+B biological assay can be used to provide further information about the channel A biological assay.

In summary, the present invention affords the possibility of a broad range of hybrid (or conventional) multiplex concepts, including (1) multiple reaction vessels in the same isolation channel, functionalized with different loading densities to extend the dynamic range; (2) multiple reaction vessels with different inner diameters, in the same isolation channel, to introduce different reaction kinetics; (3) multiple reaction vessels having positive and negative controlled reaction vessels in the same isolation channel; (4) multiple reaction vessels with different capture moieties in the same isolation channel, for the purpose of providing a multiplexed (conventional) reaction; and (5) multiple reaction vessels to conduct monoplex and multiplex reactions so that the results may be compared.

The scope of the invention is also intended to include other types or kinds of assays, including a chemical assay or a biological assay, either now known or later developed in the future.

FIG. 7

Figure 7:
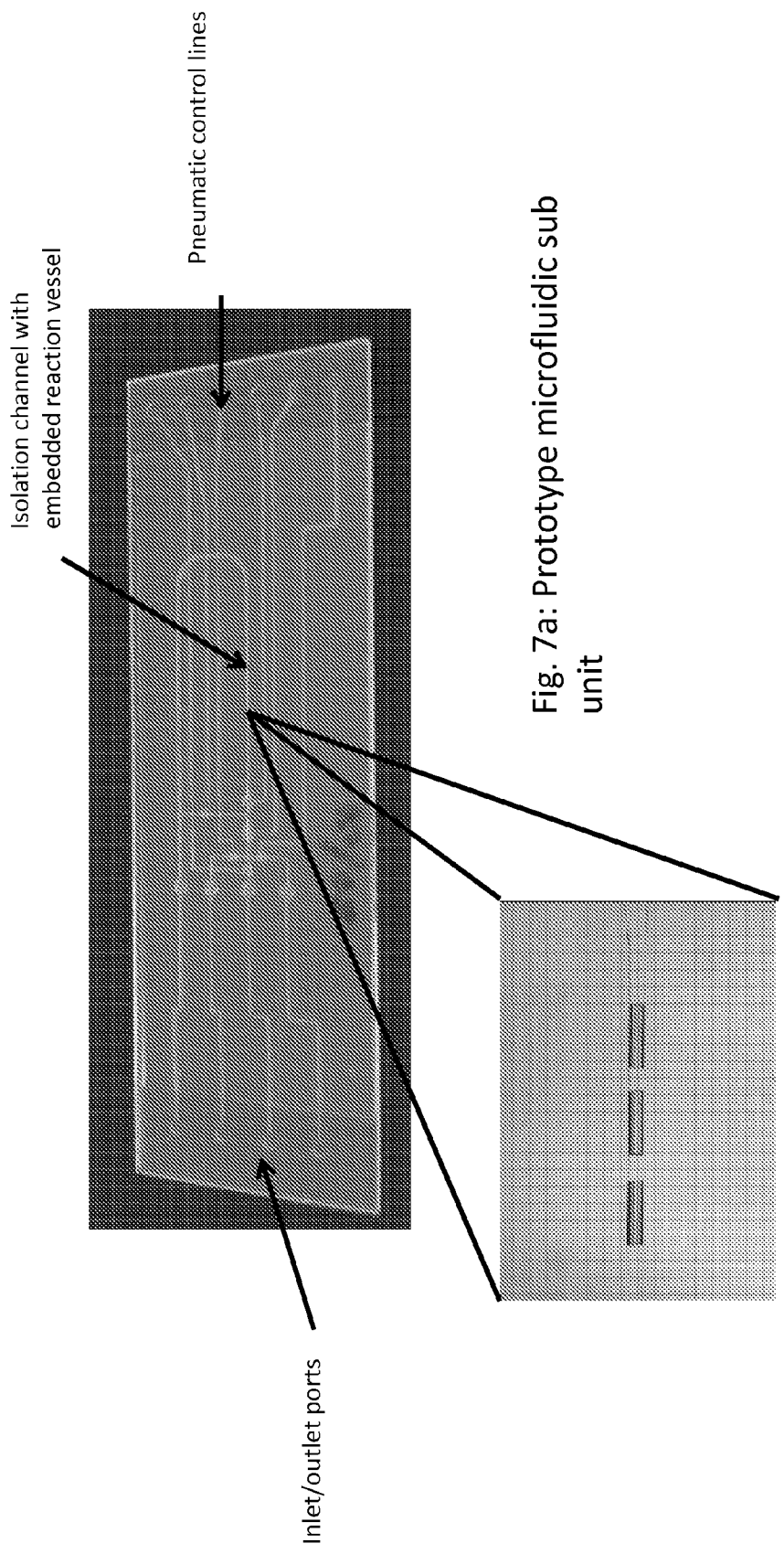
FIG. 7 includes the following.

In FIGS. 7a and 7b, a microfluidic chip consisting of fluidic channels, including isolation with three embedded reaction vessels, pneumatic control lines and inlet/outlet ports, where the three reaction vessels are embedded in isolation channel. By way of example, the reaction vessels are about 500 microns long, have an outer diameter (OD)=about 150 um, and have an inner diameter (ID)=about 30 um.

FIGS. 7c(1) and 7c(2) show the real-time signal evolution due to binding of secondary Ab (IL6) to previously captured antigen inside 3 embedded reaction vessels, and fluorescence images of three embedded reaction vessels taken 15 minutes after flowing detection Ab through the isolation channel and the embedded reaction vessel.

Figure 7D:
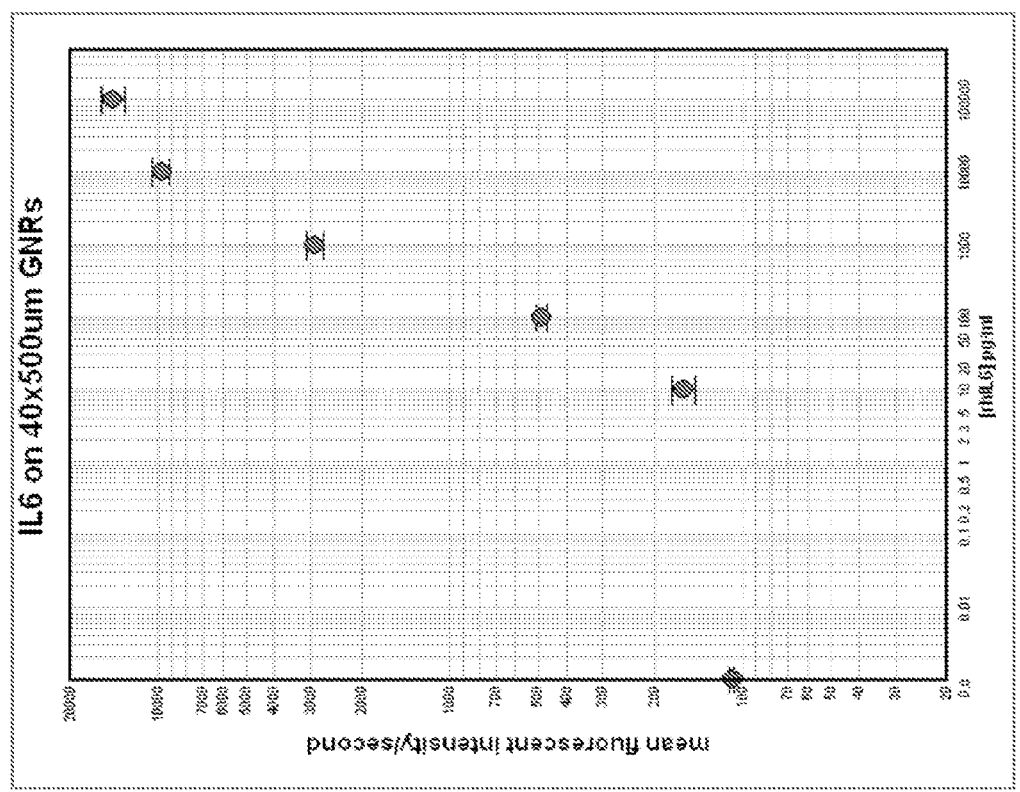
FIG. 7d shows a graph of mean fluorescent intensity per second versus IL6 in picograms/millilitre related to dose response curves for an IL6 sandwich assay performed on reaction vessels in batch mode.

FIG. 7d shows dose response curves for an IL6 sandwich assay performed on the reaction vessels in batch mode. Each data point represents a subset of reaction vessels, take from the same original batch of reaction vessels, but mixed with different IL6 antigen concentrations ranging from 0 pg/ml to 100,000 pg/ml. Clearly shown is the response to the changing concentration of antigen. This batch mode process would be used to both characterize a particular set of reaction vessels and verify the quality of the batch on the very inexpensive component.

Advantages of embedded reaction vessels include the following:

(1) Reaction vessels are made by dicing long strands of hollow glass tubing with the preferred outer and inner dimension into short sections of approximately 100-500 um long.

(2) Because the glass starting material is made with optical fiber manufacturing process, which have been highly optimized over the last 2 decades, and diced with precision diamond cutting machines, dimension control of the reaction vessels are quite excellent.

(3) Because the inside of the reaction vessel is functionalized in a batch process, meaning that up to 1000's of vessels at once are coated with the same solution of Ab, tight statistical control of the active binding moiety can be achieved.

(4) Large batches of reaction vessels means that stringent quality control and characterization of the active element of the biological assay can be performed at very low cost and with high statistical significance.

(5) The inside of the reaction vessels is protected by the outside surface which enables facile and robust techniques for picking up and placing the reaction vessels into the isolation channels without risk of damaging the fragile surface.

FIG. 8

FIG. 8 shows the hollow element may be configured as a honeycomb with multiple axial cavities or chambers that provides, when functionalized, a highly increased surface to volume ratio when compared to a reaction vessel having a single axial cavity or chamber affording the benefit of higher reaction kinetics and that also provides increased signal interrogation for the same effective volume.

The Microfluidic Technology

By way of example, the term "microfluidics" is generally understood to mean or deal with the behavior, precise control and manipulation of fluids that are geometrically constrained to a small, typically sub-millimeter, scale. In the present application, the microfluidic technology described herein is intended to include technology dimensioned in a range of about 20 micron to about 1000 microns, although the scope of the invention is not intended to be limited to any particular range.

The Scope Of The Invention

Embodiments shown and described in detail herein are provided by way of example only; and the scope of the invention is not intended to be limited to the particular configurations, dimensionalities, and/or design details of these parts or elements included herein. In other words, a person skilled in the art would appreciate that design changes to these embodiments may be made and such that the resulting embodiments would be different than the embodiments disclosed herein, but would still be within the overall spirit of the present invention.

It should be understood that, unless stated otherwise herein, any of the features, characteristics, alternatives or modifications described regarding a particular embodiment herein may also be applied, used, or incorporated with any other embodiment described herein. Also, the drawing herein are not drawn to scale.

Although the invention has been described and illustrated with respect to exemplary embodiments thereof, the foregoing and various other additions and omissions may be made therein and thereto without departing from the spirit and scope of the present invention.

What we claim is:

1. An apparatus for performing an assay, including a chemical biological or biochemical assay, on a sample comprising:
    a microfluidic assay cartridge or device that contains at least one sample inlet well configured to receive a sample;
    a microfluidic sub-unit associated with the microfluidic assay cartridge or device comprising microfluidic channels, micro-valves and at least one hollow element, the at least one hollow element being disposed within a channel and being functionalized on its inside surface with a capture moiety or molecules so as to form at least one reaction vessel;
    the microfluidic channels and micro-valves configured to respond to signaling containing information about performing the assay and to controllably receive the sample and at least one reagent through the at least one reaction vessel, and to provide from the at least one reaction vessel light containing information about the assay performed on the sample inside the at least one reaction vessel as a result of said at least one reagent;
    wherein the hollow element forming the reaction vessel is a section of long strands of hollow glass tubing of 100 to 500 microns in length, the reaction vessels having been functionalized on their inside surface in a batch process in which a plurality of the reaction vessels are coated at once with the same solution of the capture moiety;
    wherein free space exists between the outside of the hollow element forming the reaction vessel and the walls of the microfluidic channels; and
    wherein the assay cartridge contains the at least one hollow element within a channel having a piston associated with micro-valves forming a pump.

2. An apparatus according to claim 1, wherein the microfluidic channels and micro-valves are configured to respond to the signaling containing information about performing the assay and to introduce into the at least one reaction vessel one or more of the following:
    assay reagents, including a plurality of assay reagents, including labeled antibodies, and
    reagents, including an enzymatic substrate, for producing an emitted signal, and
    the at least one reaction vessel configured to allow reactions to take place for performing the assay.

3. An apparatus according to claim 2, wherein the microfluidic channels and micro-valves are configured to respond to the signaling containing information about performing the assay and to introduce into the at least one reaction vessel a wash solution to remove any non-specifically bound proteins or antibodies.

4. An apparatus according to claim 1, wherein the microfluidic sub-unit is configured to contain the assay reagents, including the at least one reagent, such as labeled antibodies; or the microfluidic sub-unit is configured to contain the reagents such as an enzymatic substrate for producing the emitted signal; or the microfluidic sub-unit is configured to contain the wash solution to remove any non-specifically bound proteins or antibodies, or some combination thereof.

5. An apparatus according to claim 3, wherein the apparatus comprises an on-board waste receptacle that is configured to capture the wash solution, along with non-specifically bound proteins or antibodies.

6. An apparatus according to claim 1, wherein the microfluidic assay cartridge is disposable.

7. An apparatus according to claim 1, wherein the apparatus comprises a detection system configured to respond to the emitted signal, and provide a detection system signal containing information about the assay performed.

8. An apparatus according to claim 1, wherein the apparatus comprises a controller configured to execute a computer program code and to provide the signaling to the microfluidic channels and micro-valves in order to perform the assay.

9. An apparatus according to claim 1, wherein each of the plurality of microfluidic channels that comprise the microfluidic sub unit, corresponds to a respective one of the at least one sample inlet well, and wherein the microfluidic channels are fluidicly isolatable from each other.

10. A microfluidic assay cartridge or device for performing an assay, including a chemical or biological assay, on a sample, comprising:
    at least one sample inlet well configured to receive a sample;
    microfluidic channels fluidicly connected to the sample well, at least one of the channels having a piston and associated micro-valves forming a pump and at least one hollow element, the at least one hollow element being functionalized on its inside surface with a capture moiety or molecules so as to form at least one reaction vessel;
    the microfluidic channels, micro-valves, and pistons configured to respond to signaling containing information about performing the assay and to controllably receive the sample and at least one reagent through the at least one reaction vessel, and to provide from the at least one reaction vessel light containing information about the assay performed on the sample inside the at least one reaction vessel as a result of said at least one reagent;
    wherein the hollow element forming the reaction vessel is a section of long strands of hollow tubing that has been cut to 100 to 500 microns in length, the reaction vessels then being functionalized on their inside surface in a batch process in which a plurality of the reaction vessels are coated at once with the same solution of the capture moiety; and wherein free space exists between the outside of the hollow element forming the reaction vessel and the walls of the microfluidic channels.

11. An apparatus according to claim 10, wherein the at least one hollow element is functionalized with the capture moiety or molecules on an inner tubular surface, an outer tubular surface or both surfaces so as to form at least one separate and fluidicly-isolated reaction vessel.

12. An apparatus according to claim 10, where the at least one reaction vessel is contained within a fluidicly-isolated channel.

13. An apparatus according to claim 1, where the at least one hollow element is configured as a honeycomb with multiple axial cavities or chambers.

14. An apparatus for performing an assay, including a chemical or biological assay, on a sample, comprising:
    at least one sample inlet well configured to receive a sample;

microfluidic channels fluidically connected to the sample well, at least one of the channels having a piston and associated micro-valves forming a pump and at least one hollow element, the at least one hollow element being functionalized on its inside surface with a capture moiety or molecules so as to form at least one reaction vessel;

the microfluidic channels, micro-valves, and pistons configured to respond to signaling containing information about performing the assay and to controllably receive the sample and at least one reagent through the at least one reaction vessel, and to provide from the at least one reaction vessel light containing information about the assay performed on the sample inside the at least one reaction vessel as a result of said at least one reagent;

the microfluidic channels and micro-valves configured to allow the channels to be fluidically isolated from each other; and wherein the hollow element forming the reaction vessel is a section of long strands of hollow tubing that has been cut to 100 to 500 microns in length, the reaction vessels then being functionalized on their inside surface in a batch process in which a plurality of the reaction vessels are coated at once with the same solution of the capture moiety.

* * * * *